United States Patent
Forsell

(10) Patent No.: US 8,313,423 B2
(45) Date of Patent: *Nov. 20, 2012

(54) HYDRAULIC ANAL INCONTINENCE TREATMENT

(76) Inventor: Peter Forsell, Bouveret (CH)

( * ) Notice: Subject to any disclaimer, the term of this patent is extended or adjusted under 35 U.S.C. 154(b) by 893 days.

This patent is subject to a terminal disclaimer.

(21) Appl. No.: 11/798,107

(22) Filed: May 10, 2007

(65) Prior Publication Data

US 2007/0232848 A1 Oct. 4, 2007

Related U.S. Application Data

(63) Continuation of application No. 10/269,950, filed on Oct. 15, 2002, now Pat. No. 7,235,044, which is a continuation of application No. 09/503,483, filed on Feb. 14, 2000, now Pat. No. 6,482,145.

(51) Int. Cl.
*A61F 2/00* (2006.01)

(52) U.S. Cl. .......................................................... 600/29

(58) Field of Classification Search .............. 600/38–41, 600/29–32; 128/DIG. 25
See application file for complete search history.

(56) References Cited

U.S. PATENT DOCUMENTS

| | | | |
|---|---|---|---|
| 2,060,913 A | 11/1936 | Weaver | |
| 2,795,641 A | 6/1957 | Frederick | |
| 3,209,081 A | 9/1965 | Ducote et al. | |
| 3,598,287 A | 8/1971 | De Man | |
| 3,662,758 A | 5/1972 | Glover | |
| 3,692,027 A | 9/1972 | Ellinwood, Jr. | |
| 3,731,679 A | 5/1973 | Wilhelmson et al. | |
| 3,731,681 A | 5/1973 | Blackshear et al. | |
| 3,750,194 A | 8/1973 | Summers | |
| 3,817,237 A | 6/1974 | Bolduc | |
| 3,855,122 A | 12/1974 | Bourganel | |
| 3,863,622 A | 2/1975 | Buuck | |
| 3,875,928 A | 4/1975 | Angelchik | |
| 3,923,060 A | 12/1975 | Ellinwood, Jr. | |
| 3,954,102 A | 5/1976 | Buuck | |
| 4,003,379 A | 1/1977 | Ellinwood, Jr. | |
| 4,009,711 A | 3/1977 | Uson | |
| 4,026,305 A | 5/1977 | Brownlee et al. | |
| 4,044,401 A | 8/1977 | Guiset | |
| 4,201,202 A | 5/1980 | Finney et al. | |
| 4,221,219 A | 9/1980 | Tucker | |
| 4,235,222 A | 11/1980 | Ionescu | |
| 4,243,306 A | 1/1981 | Bonini | |
| 4,246,893 A | 1/1981 | Berson | |
| 4,265,241 A | 5/1981 | Portner et al. | |

(Continued)

FOREIGN PATENT DOCUMENTS

DE 19511998 10/1996

(Continued)

OTHER PUBLICATIONS

International Search Report from corresponding International Application No. PCT/SE01/00306, mailed Jun. 25, 2001.

(Continued)

*Primary Examiner* — John Lacyk
(74) *Attorney, Agent, or Firm* — Nixon & Vanderhye PC

(57) ABSTRACT

An anal incontinence treatment apparatus and method includes and uses an adjustable restriction device implanted in a patient, who suffers from anal incontinence. The restriction device engages the rectum of the patient to restrict the fecal passageway. An adjustment device is adapted to adjust the restriction device such that the rectum is temporarily released, in order to open the fecal passageway when the patient wishes to achieve defaecation.

117 Claims, 12 Drawing Sheets

U.S. PATENT DOCUMENTS

| | | |
|---|---|---|
| 4,271,827 A | 6/1981 | Angelchik |
| 4,274,407 A | 6/1981 | Scarlett |
| 4,303,225 A | 12/1981 | Freeman |
| 4,304,225 A | 12/1981 | Freeman |
| 4,318,396 A | 3/1982 | Finney |
| 4,342,308 A | 8/1982 | Trick |
| 4,369,771 A | 1/1983 | Trick |
| 4,400,169 A | 8/1983 | Stephens |
| 4,412,530 A | 11/1983 | Burton |
| 4,424,807 A | 1/1984 | Evans |
| 4,505,710 A | 3/1985 | Collins |
| 4,509,947 A | 4/1985 | Lattin |
| 4,542,753 A | 9/1985 | Brenman et al. |
| 4,550,720 A | 11/1985 | Trick |
| 4,556,050 A | 12/1985 | Hodgson et al. |
| 4,559,930 A | 12/1985 | Cobiski |
| 4,559,939 A | 12/1985 | Cobiski |
| 4,563,175 A | 1/1986 | LaFond |
| 4,583,523 A | 4/1986 | Kleinke et al. |
| 4,584,994 A | 4/1986 | Bamberger et al. |
| 4,592,339 A | 6/1986 | Kuzmak et al. |
| 4,592,355 A | 6/1986 | Antebi |
| 4,599,081 A | 7/1986 | Cohen |
| 4,602,621 A | 7/1986 | Hakky |
| 4,610,658 A | 9/1986 | Buchwald et al. |
| 4,623,350 A | 11/1986 | Lapeyre et al. |
| 4,628,928 A | 12/1986 | Lowell |
| 4,664,100 A | 5/1987 | Rudloff |
| 4,677,534 A | 6/1987 | Okochi |
| 4,679,560 A | 7/1987 | Galbraith |
| 4,696,288 A | 9/1987 | Kuzmak et al. |
| 4,711,231 A | 12/1987 | Finegold et al. |
| 4,723,538 A | 2/1988 | Stewart et al. |
| 4,756,949 A | 7/1988 | Spence et al. |
| 4,771,780 A | 9/1988 | Sholder |
| 4,828,544 A | 5/1989 | Lane et al. |
| 4,828,990 A | 5/1989 | Higashi et al. |
| 4,829,990 A | 5/1989 | Thuroff et al. |
| 4,846,794 A | 7/1989 | Hertzer |
| 4,902,279 A | 2/1990 | Schmidtz et al. |
| 4,925,443 A | 5/1990 | Heilman et al. |
| 4,941,461 A | 7/1990 | Fischell |
| 4,942,668 A | 7/1990 | Franklin |
| 4,958,630 A | 9/1990 | Rosenbluth et al. |
| 4,979,955 A | 12/1990 | Smith |
| 4,982,731 A | 1/1991 | Lue et al. |
| 4,983,177 A | 1/1991 | Wolf |
| 5,006,106 A | 4/1991 | Angelchik |
| 5,012,822 A | 5/1991 | Schwarz |
| 5,042,084 A | 8/1991 | Daly |
| 5,048,511 A | 9/1991 | Rosenbluth et al. |
| 5,057,075 A | 10/1991 | Moncrief et al. |
| 5,062,416 A | 11/1991 | Stucks |
| 5,074,868 A | 12/1991 | Kuzmak |
| 5,098,369 A | 3/1992 | Heilman et al. |
| 5,112,202 A | 5/1992 | Oshima et al. |
| 5,123,428 A | 6/1992 | Schwarz |
| 5,160,338 A | 11/1992 | Vincent |
| 5,226,429 A | 7/1993 | Kuzmak |
| 5,250,020 A | 10/1993 | Bley |
| 5,297,536 A | 3/1994 | Wilk |
| 5,304,206 A | 4/1994 | Baker, Jr. et al. |
| 5,316,543 A | 5/1994 | Eberbach |
| 5,358,474 A | 10/1994 | Kaldany |
| 5,415,660 A | 5/1995 | Campbell et al. |
| 5,437,605 A | 8/1995 | Helmy |
| 5,449,368 A | 9/1995 | Kuzmak |
| 5,453,079 A | 9/1995 | Schwaninger |
| 5,454,840 A | 10/1995 | Krakovsky et al. |
| 5,501,703 A | 3/1996 | Holsheimer et al. |
| 5,505,733 A | 4/1996 | Justin et al. |
| 5,509,888 A | 4/1996 | Miller |
| 5,518,504 A | 5/1996 | Polyak |
| 5,540,731 A | 7/1996 | Testerman |
| 5,569,187 A | 10/1996 | Kaiser |
| 5,578,069 A | 11/1996 | Miner, II |
| 5,582,580 A | 12/1996 | Buckman, Jr. et al. |
| 5,665,065 A | 9/1997 | Colman et al. |
| 5,676,674 A | 10/1997 | Bolanos et al. |
| 5,690,108 A | 11/1997 | Chakeres |
| 5,702,431 A | 12/1997 | Wang et al. |
| 5,704,893 A | 1/1998 | Timm |
| 5,735,887 A | 4/1998 | Barreras et al. |
| 5,749,909 A | 5/1998 | Schroppel et al. |
| 5,769,877 A | 6/1998 | Barreras |
| 5,771,903 A | 6/1998 | Jakobsson |
| 5,814,020 A | 9/1998 | Gross |
| 5,823,991 A | 10/1998 | Shim |
| 5,827,286 A | 10/1998 | Incavo et al. |
| 5,848,962 A | 12/1998 | Feindt et al. |
| 5,858,001 A | 1/1999 | Tsals et al. |
| 5,876,425 A | 3/1999 | Gord et al. |
| 5,900,909 A | 5/1999 | Parulski et al. |
| 5,902,336 A | 5/1999 | Mishkin |
| 5,910,149 A | 6/1999 | Kuzmak |
| 5,928,195 A | 7/1999 | Malamud et al. |
| 5,938,584 A | 8/1999 | Ardito et al. |
| 5,938,669 A | 8/1999 | Klaiber et al. |
| 5,954,715 A | 9/1999 | Harrington et al. |
| 5,964,789 A | 10/1999 | Karsdon |
| 5,978,712 A | 11/1999 | Suda et al. |
| 5,995,874 A | 11/1999 | Borza |
| 5,997,501 A | 12/1999 | Gross et al. |
| 6,003,736 A | 12/1999 | Ljunggren |
| 6,067,991 A | 5/2000 | Forsell |
| 6,074,341 A | 6/2000 | Anderson et al. |
| 6,077,215 A | 6/2000 | Leysieffer |
| 6,095,968 A | 8/2000 | Snyders |
| 6,102,887 A | 8/2000 | Altman |
| 6,102,922 A | 8/2000 | Jakobsson et al. |
| 6,113,574 A | 9/2000 | Spinello |
| 6,116,193 A | 9/2000 | Goeckner |
| 6,117,067 A | 9/2000 | Gil-Vernet |
| 6,134,470 A | 10/2000 | Hartlaub |
| 6,135,945 A | 10/2000 | Sultan |
| 6,145,505 A | 11/2000 | Nikolchev et al. |
| 6,162,238 A | 12/2000 | Kaplan et al. |
| 6,185,452 B1 | 2/2001 | Schulman et al. |
| 6,197,055 B1 | 3/2001 | Matthews |
| 6,210,347 B1 | 4/2001 | Forsell |
| 6,221,060 B1 | 4/2001 | Willard |
| 6,233,474 B1 | 5/2001 | Lemelson |
| 6,275,737 B1 | 8/2001 | Mann |
| 6,319,191 B1 | 11/2001 | Sayet et al. |
| 6,332,466 B1 | 12/2001 | Yoon |
| 6,346,099 B1 | 2/2002 | Altman |
| 6,436,054 B1 | 8/2002 | Viola et al. |
| 6,450,173 B1 | 9/2002 | Forsell |
| 6,450,946 B1 | 9/2002 | Forsell |
| 6,453,907 B1 | 9/2002 | Forsell |
| 6,454,698 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,456,883 B1 | 9/2002 | Torgerson et al. |
| 6,460,543 B1 | 10/2002 | Forsell |
| 6,461,292 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |
| 6,471,635 B1 | 10/2002 | Forsell |
| 6,475,136 B1 | 11/2002 | Forsell |
| 6,482,145 B1 | 11/2002 | Forsell |
| 6,503,189 B1 | 1/2003 | Forsell |
| 6,571,127 B1 | 5/2003 | Ben-Haim et al. |
| 6,572,585 B2 | 6/2003 | Choi |
| 6,589,229 B1 | 7/2003 | Connelly et al. |
| 6,638,208 B1 | 10/2003 | Natarajan et al. |
| 6,638,303 B1 | 10/2003 | Campbell |
| 6,659,936 B1 | 12/2003 | Furness et al. |
| 6,678,561 B2 | 1/2004 | Forsell |
| 6,689,085 B1 | 2/2004 | Rubenstein et al. |
| 6,709,385 B2 | 3/2004 | Forsell |
| 6,740,075 B2 | 5/2004 | Lebel et al. |
| 6,772,011 B2 | 8/2004 | Dolgin |
| 6,895,280 B2 | 5/2005 | Meadows et al. |

| Patent No. | Date | Name |
|---|---|---|
| 6,911,002 B2 | 6/2005 | Fierro |
| 6,915,165 B2 | 7/2005 | Forsell |
| 6,948,918 B2 | 9/2005 | Hansen |
| 6,953,429 B2 | 10/2005 | Forsell |
| 6,960,233 B1 | 11/2005 | Berg et al. |
| 7,011,624 B2 | 3/2006 | Forsell |
| 7,017,583 B2 | 3/2006 | Forsell |
| 7,043,295 B2 | 5/2006 | Starkebaum |
| 7,066,922 B2 | 6/2006 | Angel et al. |
| 7,108,686 B2 | 9/2006 | Burke et al. |
| 7,207,936 B2 | 4/2007 | Forsell |
| 7,235,044 B2 | 6/2007 | Forsell |
| 7,238,165 B2 | 7/2007 | Vincent |
| 7,250,037 B2 | 7/2007 | Shermer et al. |
| 7,311,690 B2 | 12/2007 | Burnett |
| 7,338,437 B2 | 3/2008 | Forsell |
| 7,367,938 B2 | 5/2008 | Forsell |
| 7,371,208 B2 | 5/2008 | Forsell |
| 7,395,822 B1 | 7/2008 | Burton et al. |
| 7,407,479 B2 | 8/2008 | Forsell |
| 7,407,481 B2 | 8/2008 | Forsell |
| 7,442,165 B2 | 10/2008 | Forsell |
| 7,455,663 B2 | 11/2008 | Bikovsky |
| 7,569,050 B2 | 8/2009 | Moberg et al. |
| 7,621,863 B2 | 11/2009 | Forsell |
| 7,648,455 B2 | 1/2010 | Forsell |
| 7,666,132 B2 | 2/2010 | Forsell |
| 7,669,601 B2 | 3/2010 | Tal |
| 7,846,160 B2 | 12/2010 | Payne et al. |
| 7,972,354 B2 | 7/2011 | Prestezog et al. |
| 7,987,853 B2 | 8/2011 | Swann et al. |
| 2001/0011543 A1 | 8/2001 | Forsell |
| 2001/0016738 A1 | 8/2001 | Harrington et al. |
| 2002/0022759 A1 | 2/2002 | Forsell |
| 2002/0028980 A1 | 3/2002 | Thierfelder et al. |
| 2002/0040208 A1 | 4/2002 | Flaherty et al. |
| 2002/0055711 A1 | 5/2002 | Lavi et al. |
| 2002/0072759 A1 | 6/2002 | Fry |
| 2002/0095139 A1 | 7/2002 | Keogh et al. |
| 2002/0095164 A1 | 7/2002 | Andreas et al. |
| 2002/0151922 A1 | 10/2002 | Hogendijk et al. |
| 2002/0165575 A1 | 11/2002 | Saleh |
| 2002/0183588 A1 | 12/2002 | Fierro |
| 2003/0009221 A1 | 1/2003 | Forsell |
| 2003/0014010 A1 | 1/2003 | Carpenter et al. |
| 2003/0014086 A1 | 1/2003 | Sharma |
| 2003/0021822 A1 | 1/2003 | Lloyd |
| 2003/0032855 A1 | 2/2003 | Shahinpoor |
| 2003/0032857 A1 | 2/2003 | Forsell |
| 2003/0050591 A1 | 3/2003 | McHale |
| 2003/0055442 A1 | 3/2003 | Laufer et al. |
| 2003/0060893 A1 | 3/2003 | Forsell |
| 2003/0066536 A1 | 4/2003 | Forsell |
| 2003/0069547 A1 | 4/2003 | Gonon |
| 2003/0088148 A1 | 5/2003 | Forsell |
| 2003/0092962 A1 | 5/2003 | Forsell |
| 2003/0100929 A1 | 5/2003 | Forsell |
| 2003/0105385 A1 | 6/2003 | Forsell |
| 2003/0109771 A1 | 6/2003 | Forsell |
| 2003/0125605 A1 | 7/2003 | Forsell |
| 2003/0125768 A1 | 7/2003 | Forsell |
| 2003/0144648 A1 | 7/2003 | Forsell |
| 2003/0163029 A1 | 8/2003 | Sonnenschein et al. |
| 2003/0208247 A1 | 11/2003 | Spinelli et al. |
| 2003/0233143 A1 | 12/2003 | Gharib et al. |
| 2004/0024419 A1 | 2/2004 | Slepian et al. |
| 2004/0034275 A1 | 2/2004 | Forsell |
| 2004/0068299 A1 | 4/2004 | Laske et al. |
| 2004/0089313 A1 | 5/2004 | Utley et al. |
| 2004/0102804 A1 | 5/2004 | Chin |
| 2004/0122526 A1 | 6/2004 | Imran |
| 2004/0122527 A1 | 6/2004 | Imran |
| 2004/0147871 A1 | 7/2004 | Burnett |
| 2004/0162568 A1 | 8/2004 | Saadat et al. |
| 2004/0177918 A1 | 9/2004 | Murata et al. |
| 2004/0249451 A1 | 12/2004 | Lu et al. |
| 2004/0260316 A1 | 12/2004 | Knudson et al. |
| 2005/0038484 A1 | 2/2005 | Knudson et al. |
| 2005/0055025 A1 | 3/2005 | Zacouto et al. |
| 2005/0075697 A1 | 4/2005 | Olson et al. |
| 2005/0209633 A1 | 9/2005 | Callister et al. |
| 2005/0240229 A1 | 10/2005 | Whitehurst et al. |
| 2005/0245957 A1 | 11/2005 | Starkebaum et al. |
| 2005/0261712 A1 | 11/2005 | Balbierz et al. |
| 2005/0266042 A1 | 12/2005 | Tseng |
| 2005/0267405 A1 | 12/2005 | Shah |
| 2005/0267596 A1 | 12/2005 | Chen et al. |
| 2006/0069414 A1 | 3/2006 | Imran et al. |
| 2006/0127246 A1 | 6/2006 | Forsell |
| 2006/0142635 A1 | 6/2006 | Forsell |
| 2006/0149124 A1 | 7/2006 | Forsell |
| 2006/0149129 A1 | 7/2006 | Watts et al. |
| 2006/0167539 A1 | 7/2006 | McEwan |
| 2006/0212055 A1 | 9/2006 | Karabey et al. |
| 2006/0224177 A1 | 10/2006 | Finitsis |
| 2006/0229688 A1 | 10/2006 | McClure et al. |
| 2006/0235482 A1 | 10/2006 | Forsell |
| 2006/0257446 A1 | 11/2006 | Tropsha et al. |
| 2007/0015959 A1 | 1/2007 | Forsell |
| 2007/0038232 A1 | 2/2007 | Kraemer |
| 2007/0049790 A1 | 3/2007 | Wagner et al. |
| 2007/0073099 A1 | 3/2007 | Forsell |
| 2007/0092862 A1 | 4/2007 | Gerber |
| 2007/0156204 A1 | 7/2007 | Denker et al. |
| 2007/0167670 A1 | 7/2007 | Coleman et al. |
| 2007/0193632 A1 | 8/2007 | Shu |
| 2007/0225802 A1 | 9/2007 | Forsell |
| 2007/0232848 A1 | 10/2007 | Forsell |
| 2007/0233019 A1 | 10/2007 | Forsell |
| 2007/0250020 A1 | 10/2007 | Kim et al. |
| 2007/0265675 A1 | 11/2007 | Lund et al. |
| 2008/0004487 A1 | 1/2008 | Haverfiled |
| 2008/0045783 A1 | 2/2008 | Forsell |
| 2008/0051718 A1 | 2/2008 | Kavazov et al. |
| 2008/0086179 A1 | 4/2008 | Sharma |
| 2008/0103544 A1 | 5/2008 | Weiner |
| 2008/0154256 A1 | 6/2008 | Payne et al. |
| 2008/0178889 A1 | 7/2008 | Tal |
| 2008/0200753 A1 | 8/2008 | Forsell |
| 2008/0214888 A1 | 9/2008 | Shalom |
| 2008/0245371 A1 | 10/2008 | Gruber |
| 2008/0269548 A1 | 10/2008 | Vecchiotti et al. |
| 2008/0275296 A1 | 11/2008 | Forsell |
| 2009/0018388 A1 | 1/2009 | Forsell |
| 2009/0024108 A1 | 1/2009 | Lee-Sepsick et al. |
| 2009/0054725 A1 | 2/2009 | Forsell |
| 2009/0131959 A1 | 5/2009 | Rolland |
| 2009/0240100 A1 | 9/2009 | Forsell |
| 2009/0240294 A1 | 9/2009 | Forsell |
| 2009/0247817 A1 | 10/2009 | Forsell |
| 2009/0247818 A1 | 10/2009 | Forsell |
| 2009/0248033 A1 | 10/2009 | Forsell |
| 2009/0250068 A1 | 10/2009 | Forsell |
| 2009/0254106 A1 | 10/2009 | Forsell |
| 2009/0266366 A1 | 10/2009 | Swann et al. |
| 2010/0145138 A1 | 6/2010 | Forsell |
| 2010/0145139 A1 | 6/2010 | Forsell |
| 2010/0217067 A1 | 8/2010 | Forsell |
| 2010/0286735 A1 | 11/2010 | Garfield et al. |
| 2010/0312047 A1 | 12/2010 | Forsell |
| 2010/0312048 A1 | 12/2010 | Forsell |
| 2010/0312049 A1 | 12/2010 | Forsell |
| 2010/0312050 A1 | 12/2010 | Forsell |
| 2010/0312163 A1 | 12/2010 | Forsell |
| 2010/0312164 A1 | 12/2010 | Forsell |
| 2010/0312356 A1 | 12/2010 | Forsell |
| 2010/0318116 A1 | 12/2010 | Forsell |
| 2010/0318117 A1 | 12/2010 | Forsell |
| 2010/0318118 A1 | 12/2010 | Forsell |
| 2010/0324360 A1 | 12/2010 | Forsell |
| 2010/0324361 A1 | 12/2010 | Forsell |
| 2010/0324362 A1 | 12/2010 | Forsell |
| 2010/0324591 A1 | 12/2010 | Forsell |
| 2010/0331614 A1 | 12/2010 | Forsell |
| 2010/0331615 A1 | 12/2010 | Forsell |
| 2010/0331616 A1 | 12/2010 | Forsell |
| 2010/0331617 A1 | 12/2010 | Forsell |
| 2010/0331945 A1 | 12/2010 | Forsell |

| | | |
|---|---|---|
| 2010/0332000 A1 | 12/2010 | Forsell |
| 2011/0009894 A1 | 1/2011 | Forsell |
| 2011/0009896 A1 | 1/2011 | Forsell |
| 2011/0009897 A1 | 1/2011 | Forsell |
| 2011/0015473 A1 | 1/2011 | Forsell |
| 2011/0015474 A1 | 1/2011 | Forsell |
| 2011/0040143 A1 | 2/2011 | Forsell |
| 2011/0172693 A1 | 7/2011 | Forsell |
| 2011/0184230 A1 | 7/2011 | Forsell |
| 2011/0192402 A1 | 8/2011 | Forsell |
| 2011/0196192 A1 | 8/2011 | Forsell |
| 2011/0196193 A1 | 8/2011 | Forsell |
| 2011/0196194 A1 | 8/2011 | Forsell |
| 2011/0196271 A1 | 8/2011 | Forsell |
| 2011/0196371 A1 | 8/2011 | Forsell |
| 2011/0196391 A1 | 8/2011 | Forsell |
| 2011/0196411 A1 | 8/2011 | Forsell |
| 2011/0196435 A1 | 8/2011 | Forsell |
| 2011/0196466 A1 | 8/2011 | Forsell |
| 2011/0196476 A1 | 8/2011 | Forsell |
| 2011/0196481 A1 | 8/2011 | Forsell |
| 2011/0196482 A1 | 8/2011 | Forsell |
| 2011/0196483 A1 | 8/2011 | Forsell |
| 2011/0196484 A1 | 8/2011 | Forsell |
| 2011/0196485 A1 | 8/2011 | Forsell |
| 2011/0196486 A1 | 8/2011 | Forsell |
| 2011/0196505 A1 | 8/2011 | Forsell |
| 2011/0196506 A1 | 8/2011 | Forsell |
| 2011/0201870 A1 | 8/2011 | Forsell |
| 2011/0201871 A1 | 8/2011 | Forsell |
| 2011/0201873 A1 | 8/2011 | Forsell |
| 2011/0202041 A1 | 8/2011 | Forsell |
| 2011/0202129 A1 | 8/2011 | Fofsell |
| 2011/0202131 A1 | 8/2011 | Forsell |
| 2011/0208231 A1 | 8/2011 | Forsell |
| 2011/0218394 A1 | 9/2011 | Forsell |
| 2011/0224787 A1 | 9/2011 | Forsell |
| 2011/0230930 A1 | 9/2011 | Forsell |
| 2011/0263928 A1 | 10/2011 | Forsell |

FOREIGN PATENT DOCUMENTS

| | | |
|---|---|---|
| EP | 0102548 | 3/1984 |
| EP | 01 343 40 | 3/1985 |
| EP | 0 200 286 | 11/1986 |
| EP | 0300552 | 1/1989 |
| EP | 0378251 | 7/1990 |
| EP | 0412191 | 2/1991 |
| EP | 0 583 012 | 2/1994 |
| EP | 0611561 | 9/1994 |
| EP | 0626154 | 11/1994 |
| EP | 0876808 | 11/1998 |
| EP | 1 004 330 | 5/2000 |
| EP | 1 033 142 | 9/2000 |
| EP | 1 072 238 | 1/2001 |
| EP | 1 514 526 | 3/2005 |
| EP | 1563814 | 8/2005 |
| EP | 1563886 | 8/2005 |
| EP | 1 586 283 | 10/2005 |
| EP | 1598030 | 11/2005 |
| EP | 1 681 041 | 7/2006 |
| EP | 1 878 452 | 1/2008 |
| EP | 1 913 880 | 4/2008 |
| FR | 2688693 | 9/1993 |
| FR | 2692777 | 12/1993 |
| FR | 27565485 | 6/1998 |
| FR | 2797181 | 2/2001 |
| GB | 8 856 74 | 12/1961 |
| GB | 1194358 | 6/1970 |
| WO | WO 84/01282 | 4/1984 |
| WO | WO 94/27504 | 12/1994 |
| WO | WO 96/01597 | 1/1996 |
| WO | WO 96/11036 | 4/1996 |
| WO | WO 96/39932 | 12/1996 |
| WO | WO 97/41799 | 11/1997 |
| WO | WO 98/50099 | 11/1998 |
| WO | WO 99/18885 | 4/1999 |
| WO | WO 00/09048 | 2/2000 |
| WO | WO 00/15158 | 3/2000 |
| WO | WO 00/16686 | 3/2000 |
| WO | WO 01/12078 | 2/2001 |
| WO | WO 01/12108 | 2/2001 |
| WO | WO 01/45487 | 6/2001 |
| WO | WO 01/45590 | 6/2001 |
| WO | WO 01/47575 | 7/2001 |
| WO | WO 0147434 | 7/2001 |
| WO | WO 0147439 | 7/2001 |
| WO | WO 01/58391 | 8/2001 |
| WO | WO 0154615 | 8/2001 |
| WO | WO 01/67964 | 9/2001 |
| WO | WO 02/38217 | 5/2002 |
| WO | WO 02/40083 | 5/2002 |
| WO | WO 02/053210 | 7/2002 |
| WO | WO 02/058563 | 8/2002 |
| WO | WO 02/087657 | 11/2002 |
| WO | WO 02/100481 | 12/2002 |
| WO | WO 03/002192 | 1/2003 |
| WO | WO 03/033054 | 4/2003 |
| WO | WO 2004/012806 | 2/2004 |
| WO | WO 2004/018037 | 3/2004 |
| WO | WO 2004/019765 | 3/2004 |
| WO | WO 2004/060171 | 7/2004 |
| WO | WO 2004/071684 | 8/2004 |
| WO | WO 2004/101029 | 11/2004 |
| WO | WO 98/06358 | 2/2005 |
| WO | WO 2005/072169 | 8/2005 |
| WO | WO 2005/105003 | 11/2005 |
| WO | WO 2006/114004 | 11/2006 |
| WO | WO 2006/122285 | 11/2006 |
| WO | WO 2006/134106 | 12/2006 |
| WO | WO 2007/017880 | 2/2007 |
| WO | WO 2007/041795 | 4/2007 |
| WO | WO 0147435 | 4/2007 |
| WO | WO 2007/051563 | 5/2007 |
| WO | WO 2007/109759 | 9/2007 |
| WO | WO 2007/137026 | 11/2007 |
| WO | WO 2007/149555 | 12/2007 |
| WO | WO 2008/135988 | 11/2008 |
| WO | WO 2009/010799 | 1/2009 |
| WO | WO 2009/096854 | 8/2009 |
| WO | WO 2009/096865 | 8/2009 |
| WO | WO 2009/096868 | 8/2009 |
| WO | WO 2009/115645 | 9/2009 |

OTHER PUBLICATIONS

U.S. Appl. No. 09/373,224, filed Aug. 12, 1999, Forsell.
U.S. Appl. No. 11/988,450, filed May 27, 2009, Forsell.
Webster's II New River side University, 1984, pp. 573,1000.
Anand, Sneh. "Electrical Pacing of the Ampullary Isthmic Junction for Contraception", IEEE Engineering in Medicine & Biology 10th Annual International Conference, 1988.

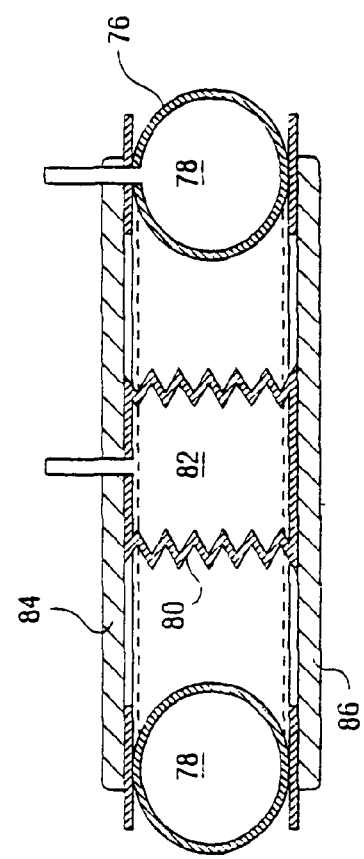
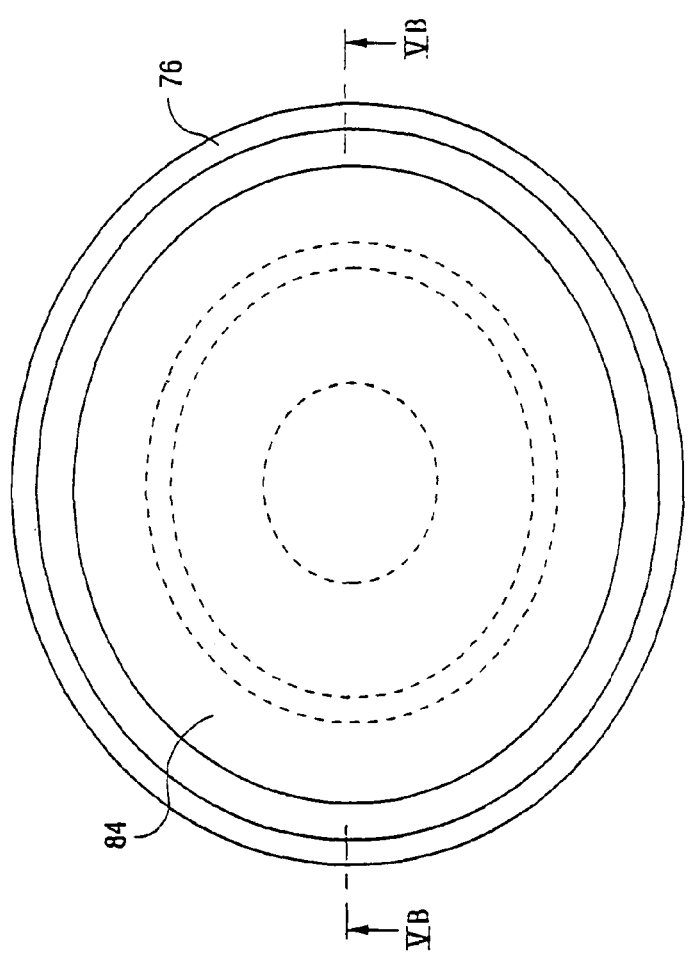
Fig. 5A
Fig. 5B

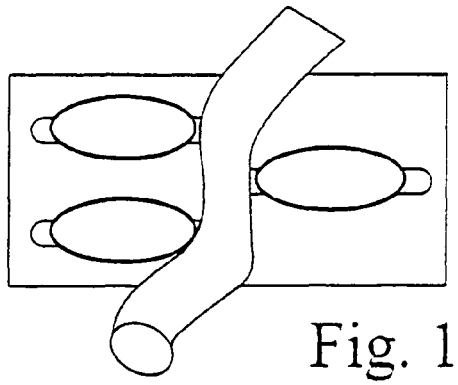 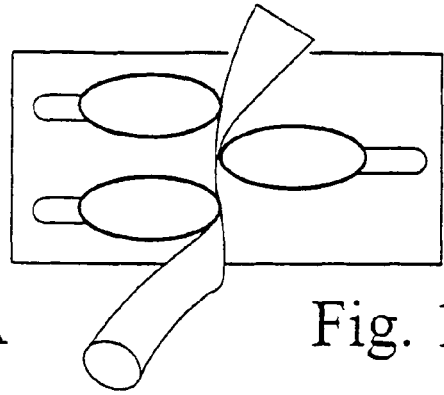
Fig. 13A  Fig. 13B
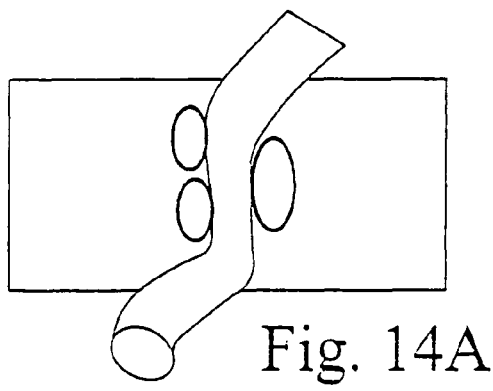 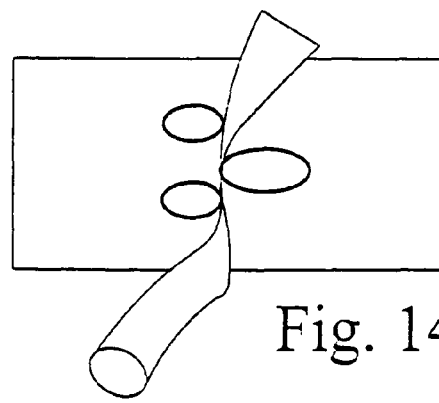
Fig. 14A  Fig. 14B
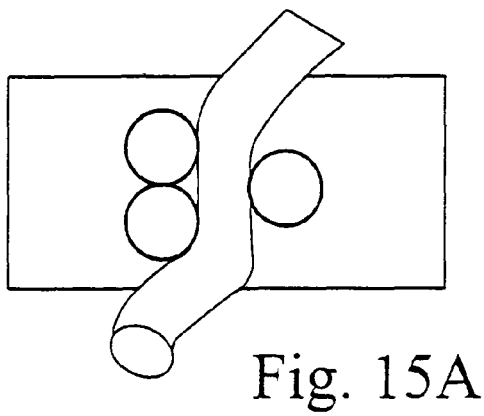 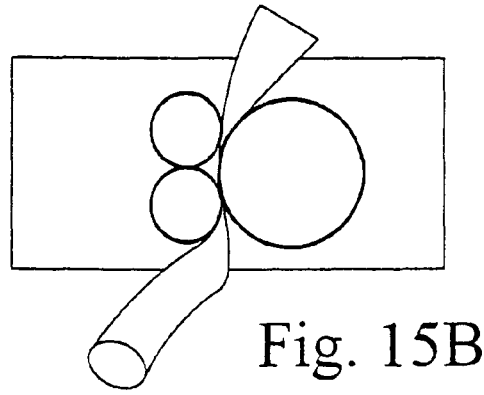
Fig. 15A  Fig. 15B

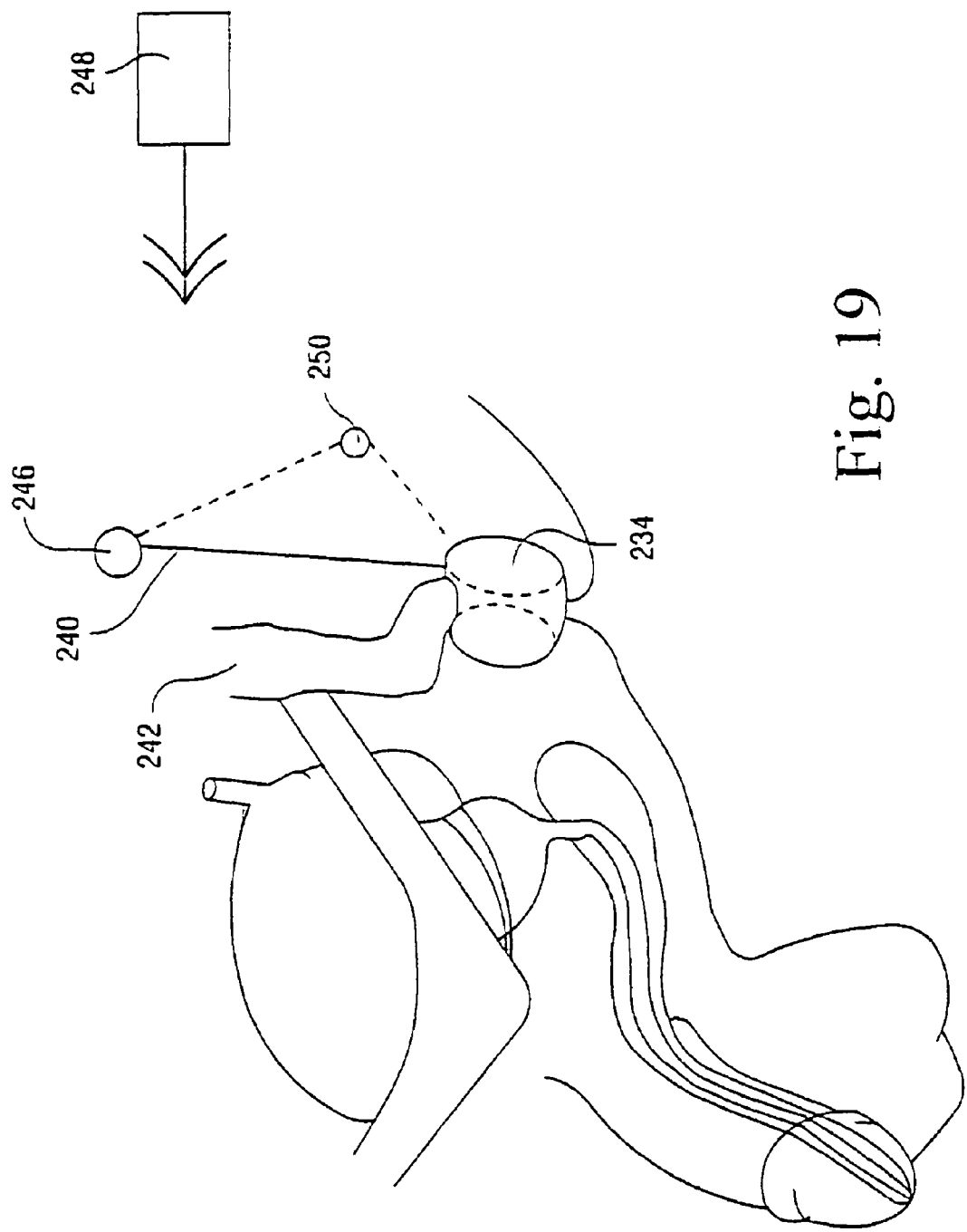

HYDRAULIC ANAL INCONTINENCE TREATMENT

CROSS REFERENCE TO RELATED APPLICATION

This application is a continuation of application Ser. No. 10/269,950, filed Oct. 15, 2002, which is a continuation of application Ser. No. 09/503,483, filed Feb. 14, 2000 (now U.S. Pat. No. 6,482,145, Issued: Nov. 19, 2002), the entire contents of which are hereby incorporated by reference in this application, and incorporates herein by reference the disclosure of provisional Application Ser. No. 60/148,345 filed Aug. 12, 1999.

BACKGROUND OF THE INVENTION

The present invention relates to an anal incontinence treatment apparatus and method. More specifically, the invention relates to an anal incontinence treatment apparatus and method for surgical application in the body of an anal incontinence patient for restricting the colon or rectum of a patient.

Anal incontinence is a widespread problem. Many different solutions to this problem have been tried. Several kinds of sphincter plastic surgery are used today to remedy anal incontinence. There is a prior manually operated sphincter system in an initial clinical trial phase with the hydraulic sphincter system connected to a reservoir placed in the scrotum. Disadvantage of this system is that hard fibrosis created around the reservoir over time may cause malfunction of pumping components. Thus, the created fibrosis will sooner or later become a hard fibrotic layer which may make it difficult to pump the reservoir. Yet a further disadvantage is that the use of hydraulic fluid always entails a risk of fluid leaking from the prosthetis. Furthermore, it is a rather complicated task to mechanically manually pump the reservoir when defaecation is needed. U.S. Pat. No. 5,593,443 discloses hydraulic anal sphincter under both reflex and voluntary control. An inflatable artificial sphincter with the pump system in scrotum is disclosed in U.S. Pat. No. 4,222,377.

SUMMARY OF THE INVENTION

A prime object of the present invention is to provide an anal incontinence treatment apparatus, which does not require manual manipulation of a combined reservoir a pump mechanism placed in the scrotum or labia majora region of the patient.

Another object of the invention is to provide an anal incontinence treatment apparatus, which does not require complicated surgery.

Yet another object of the invention is to provide an anal incontinence treatment apparatus, which may be conveniently remotely controlled by the patient.

Accordingly, the present invention provides an anal incontinence treatment apparatus, comprising an adjustable restriction device implanted in a patient, who suffers from anal incontinence, and engaging a portion of the colon or rectum of the patient to restrict the fecal passageway therein, an adjustment device which adjusts the restriction device to restrict the colon or rectum to close the fecal passageway, or release the colon or rectum to open the fecal passageway, and a powered hydraulic operation device for adjusting the adjustment device.

Preferably the hydraulic operation device adjusts the adjustment device in a non-manual manner. The expression "non-manually manner" should be understood to mean that the restriction device is not adjusted by manually touching subcutaneously implanted components of the apparatus or not manipulated by touching the skin of the patient. Preferably, the adjustment device adjusts the restriction device in a non-invasive manner. The expression powered should be understood as energised with everything without manual force, preferable electric energy.

The adjustment device may adjust the restriction device in a non-magnetic manner, i.e. magnetic forces may not be involved when adjusting the restriction device.

The adjustment device may also adjust the restriction device in a non-thermal manner, i.e. thermal energy may not be involved when adjusting the restriction device. Furthermore, as opposed to prior art anal incontinence treatment devices the adjustment device of the invention is not operated by manual forces, such as by manually compressing a fluid containing balloon implanted in the scrotum. Instead the apparatus of the invention may further comprise a powered operation device for operating the adjustment device.

In the various embodiments hereinafter described the restriction device generally forms an at least substantially closed loop. However, the restriction device may take a variety of different shapes, such as the shape of a square, rectangle or ellipse. The substantially closed loop could for example be totally flat, i.e. thin as seen in the radial direction. The shape of restriction device may also be changed during use, by rotation or movements of the restriction device in any direction.

Preferably the restriction device controls the size of the area of the fecal passageway in the colon or rectum, preferably to change steplessly with a preselected size that is satisfactory for the patient.

A control device for controlling the restriction device may conveniently be provided and may comprise an internal programmable control unit implanted in the patient and, possibly an external control unit outside the patient's body for programming the programmable internal control unit. Alternatively, the external control unit may be programmable and wirelessly control the restriction device.

At least one sensor for sensing at least one physical parameter of the patient may conveniently be implanted in the patient. The sensor preferably senses the pressure against the restriction device or the colon or rectum or other important parameters and either the internal control unit or the external control unit of the control device may suitably control the restriction device to release the fecal passage way. For safety the restrictor device may release the fecal passageway in response to the sensor sensing for example an abnormally high pressure value. The internal control unit may directly controls the restriction device in response to signals by the sensor.

The apparatus preferably comprises a control device which may comprise both an internal or an external control unit for controlling the restriction device preferable for wirelessly controlling the restriction device. Preferable the implanted internal control unit being programmable by the external control unit. The external control unit may also be programmable.

Preferably, a hydraulic operation device, suitably electrically powered, is implanted in the patient for operating the adjustment device and a reservoir is also implanted in the patient and contains a predetermined amount of hydraulic fluid, wherein the hydraulic operation device operates the adjustment device by using the hydraulic fluid of the reservoir.

In accordance with a first main embodiment of the invention, the adjustment device comprises an expandable cavity in the restriction device, the colon or rectum being squeezed upon expansion of the cavity and released upon contraction of the cavity, and the hydraulic operation device distributes hydraulic fluid from the reservoir to expand the cavity, and distributes hydraulic fluid from the cavity to the reservoir to contract the cavity.

A fluid distribution tube may readily be connected between the reservoir and the cavity in a manner so that the tube does not interfere with other implanted components of the apparatus.

Preferably, the reservoir defines a chamber for the predetermined amount of fluid and the hydraulic operation device changes the size of the chamber. The hydraulic operation device suitably comprises first and second wall portions of the reservoir, which are displaceable relative to each other to change the size of the chamber of the reservoir. The hydraulic operation device may distribute fluid from the reservoir to the cavity of the restriction member in response to a predetermined first displacement of the first wall portion of the reservoir relative to the second wall portion of the reservoir and may distribute fluid from the cavity to the reservoir in response to a predetermined second displacement of the first wall portion relative to the second wall portion.

The first and second wall portions of the reservoir may be displaceable relative to each other by manual manipulation, such as by manually pushing, pulling or rotating any of the wall portions in one direction, or alternatively, may be displaceable relative to each other by a device powered magnetically, hydraulically, or electrically (e.g. by an electric motor). In this embodiment no pump is used, only the volume of the reservoir is varied. This is of great advantage compared to the solution described below when a pump is used to pump fluid between the reservoir and the adjustment device because there is no need for a non-return valve and it is still possible to have fluid going both to and from the reservoir.

The operation device may comprise a fluid conduit, which is devoid of any non-return return valve between the pump and the cavity (including the same) and the reservoir may form part of the conduit and a fluid chamber with a variable volume. The pump may distribute fluid from the chamber to the cavity by reduction of the volume of the chamber and withdraw fluid from the cavity by expansion of the volume of the chamber. The operation device preferably comprises a motor for driving the pump, which may comprise a movable wall of the reservoir for changing the volume of the chamber. Any kind of motor could be used for the different operations as well as wireless remote solutions.

In accordance with a particular embodiment of the invention, the hydraulic operation device comprises a pump for pumping fluid between the reservoir and the cavity of the restriction device. The pump preferably comprises a first activation member for activating the pump to pump fluid from the reservoir to the cavity of the restriction device, and a second activation member for activating the pump to pump fluid from the cavity to the reservoir. The first and second activation members may be operable by manual manipulation thereof, such as by manually pushing, pulling or rotating any of the activation members in one direction. At least one of the activation members is constructed to operate when subjected to an external pressure exceeding a predetermined magnitude.

As an alternative to the manual manipulation, at least one of the first and second activating members may be operable by a device powered magnetically, hydraulically, or electrically (e.g. by an electric motor). The pump may pump fluid both to and away from the adjustment device or hydraulic device controlling the adjustment device. A mechanical solution is proposed in which it is possible to pump in both directions just by pushing an activating member in one direction. Another alternative is a pump pumping in only one direction and an adjustable valve to change the direction of fluid to either increase or decrease the amount of fluid in the reservoir. This valve may be manipulated either manually, mechanically, magnetically, or hydraulically.

Wherever a magnetic means is utilized according to the invention it may comprise a permanent magnet and a magnetic material reed switch, or other suitable known or conventional magnetic devices.

A physical lumen, like the colon or rectum or the prolongation thereof, is often easier to restrict by contracting at least two opposite or different side walls of the lumen against each other. The expression "colon or rectum or the prolongation thereof" should be understood to mean the rectum extended all the way out to the anal sphincter and following the passage of the large bowel in the other direction. It is also possible to use only one element and squeeze against human bone or tissue.

Either mechanical or hydraulic solutions may be employed to operate the restriction device. Alternatively, the restriction device may comprise an adjustable cuff, a clamp or a roller for bending the colon or rectum or the prolongation thereof to restrict the fecal passageway therein. Such a cuff, clamp or roller may also be utilized for squeezing the colon or rectum or the prolongation thereof against human material inside the body of the patient for an example the sacral bone of the patient.

Advantageously, the forming means may form the restriction member into a loop having a predetermined size.

The adjustment device may change the size of the restriction opening such that the outer circumferential confinement surface of the restriction member either is changed or is unchanged.

Preferable the restriction device comprises an elongated restriction member and forming means for forming the restriction member into at least a substantially closed loop around the colon or rectum or it's prolongation, the loop defining a restriction opening, whereby the adjustment device adjusts the restriction member in the loop to change the size of the restriction opening.

The elongated restriction member may be flexible, for example take the shape of a belt or a cord, and the adjustment device may pull a first portion of the flexible restriction member from a second portion of the flexible restriction member opposite the first portion in the loop to squeeze the colon or rectum or the prolongation thereof between two opposite lengths of the elongated flexible restriction member to restrict the fecal passageway. The restriction member may be non-inflatable, and the adjustment device may mechanically adjust the restriction member in the loop.

In accordance with a particular embodiment of the invention, the adjustment device mechanically adjusts the restriction device. Thus, the restriction device may comprise two or more elements on different sides of the colon or rectum, and the adjustment device may squeeze the colon or rectum or the prolongation thereof between the elements to restrict the fecal passageway.

In accordance with an alternative, the restriction device may comprise two articulated clamping elements positioned on opposite sides of the colon or rectum or the prolongation thereof, and the adjustment device may move the clamping elements towards each other to clamp the rectum between the clamping elements to restrict the fecal passageway.

In accordance with another alternative, the restriction device may bend the colon or rectum or the prolongation thereof. For example, the restriction device may comprise at least two bending members, such as cylindrical or hour-glass shaped rollers, positioned on opposite sides of the colon or rectum or the prolongation thereof, and the adjustment device may move the bending members against the esophagus or stomach to bend the latter to decrease the colon or rectum or the prolongation thereof in two opposite spaced apart directions to bend the colon or rectum or the prolongation thereof to restrict the fecal passageway. The bending or rotating members may have any shape or form and be either hydraulic or non-inflatable.

In accordance with another particular embodiment of the invention, the hydraulic operation device comprises a servo means, suitably including hydraulic means. Alternatively, the servo means may include magnetic or electric means. Preferably, the servo means comprises a servo reservoir defining a chamber containing servo fluid and the hydraulic operation device comprises first and second wall portions of the servo reservoir, which are displaceable relative to each other to change the size of the chamber of the servo reservoir. The same principle will apply for the servo reservoir as for the earlier described reservoir wherein the volume in the servo reservoir may be increased or decreased by a first or second displacement of the first wall portion relative to the second wall portion of the servo reservoir and thereby control the earlier described reservoir and thereby indirectly control the fecal passageway. The first and second wall portions of the servo reservoir may be displaceable relative to each other by manual manipulation, such as by manually pushing, pulling or rotating any of the wall portions of the servo reservoir in one direction. Alternatively, the first and second wall portions may be displaceable by magnetically, hydraulically or electrically powered device. These powered devices may all be activated by manual manipulating means preferable located subcutaneously. This activation may be indirect, for example via a switch.

Especially when manual manipulation means are used, the servo means is suitable to use. With servo means less force is needed for controlling the adjustment device. Hydraulic operation is preferably used with the servo means. One example is a closed system that controls another closed system in which hydraulic components of the adjustment device are incorporated. Minor changes in the amount of fluid in a reservoir of the first system could then lead to major changes in the amount of fluid in a reservoir in the second system. Consequently, the change in volume in the reservoir of the second system affects the hydraulic operation of the adjustment device which is incorporated in the second closed system. The great advantage of such a servo means is that the larger volume system could be placed at a suitable location, e.g. inside the abdomen where there is more space, and still it would be possible to use manual manipulation means of the smaller system subcutaneously. The servo reservoir could control the reservoir of the larger volume.

The servo reservoir could be controlled directly or indirectly by a small fluid supply reservoir, which may be placed subcutaneously and may be activated by manual manipulation means controlling the servo reservoir or other suitable device.

Preferably, the hydraulic operation device comprises first and second wall portions of the fluid supply reservoir, which are displaceable relative to each other to change the size of the chamber of the fluid supply reservoir. The hydraulic operation device may distribute fluid from the fluid supply reservoir to the servo reservoir in response to a predetermined first displacement of the first wall portion of the fluid supply reservoir relative to the second wall portion of the fluid supply reservoir and to distribute fluid from the servo reservoir to the fluid supply reservoir in response to a predetermined second displacement of the first wall portion relative to the second wall portion. The wall portions of the fluid supply reservoir may be displaceable relative to each other by manual manipulation means or be displaceable relative to each other by manual manipulation means for pushing, pulling, or rotating any of the wall portions of the fluid supply reservoir in one direction. Alternatively, the wall portions of the fluid supply reservoir may be displaceable relative to each other by magnetic means, hydraulic means, manually manipulated means, or electrical control means including an electric motor. The magnetic means, hydraulic means, or electrical control means may all be activated by manually manipulated means preferably located subcutaneously. This control may be indirect, for example via a switch.

Even in the broadest embodiment of the invention the adjustment device may comprise a servo means. The servo means may comprise a hydraulic means, an electric control means, a magnetic means, mechanical means, or a manual manipulating means. The hydraulic means, electric control means, mechanical means or magnetic means may be activated by manual manipulating means. Using a servo system will save the use of force when adjusting the adjustment device which may be of importance in many applications.

All systems according to the invention may be controlled by a wireless remote control.

In accordance with an advantageous embodiment of the invention, there is provided a wireless remote control for controlling the restriction device. The remote control may conveniently comprise an external hand-held remote control unit which is manually operable by the patient to control the restriction device to squeeze and release the colon or rectum or the prolongation thereof. The remote control may advantageously be capable of obtaining information on pressure or other important parameters such as the pressure against the restriction device and of commanding the operation device to operate the adjustment device to adjust the restriction device in response to obtained information. With the remote control the apparatus of the invention is conveniently controlled to adjust the implanted restriction device, which controls the restriction of the fecal passageway and wherein the restriction device is operable to open and close the fecal passageway. With the remote control the restriction device may steplessly controls the cross-sectional area of the passageway.

The apparatus of the invention may further comprise a pressure sensor for directly or indirectly sensing the pressure against the restriction device and the control device may control the restriction device in response to signals from the pressure sensor. The adjustment device preferably non-invasively adjusts the restriction device to change the size of the cross-sectional area.

The adjustment device or other energy consuming components of the apparatus may also be energised with wirelessly transmitted energy from outside the patient's body or with an implanted battery or accumulator.

The apparatus may further comprise an implanted energy transfer device, wherein the control device releases electric energy and the energy transfer transfers the electric energy directly or indirectly into kinetic energy for operation of the restriction device.

The remote control comprises means for wireless transfer of energy from outside the patient's body to energy consuming implanted components of the apparatus. A motor may suitably be implanted for operating the operation device and the means for wireless transfer of energy may directly power the motor with transferred energy. The energy transferred by the means for transfer of energy may comprise a wave signal, an electric field or a magnetic field. Preferably, the wireless remote control comprises an external signal transmitter and an implanted signal receiver. For example, the signal transmitter and signal receiver may transmit and receive a signal in the form of digital pulses, which may comprise a magnetic or electric field. Alternatively, which is preferred, the signal transmitter and signal receiver may transmit and receive a wave signal, which may comprise an electromagnetic wave signal, a sound wave signal or a carrier wave signal for a remote control signal. The receiver may comprise a control unit for controlling the hydraulic operation device in response to signals from the signal transmitter.

The apparatus of the invention may further comprise an implanted energizer unit for providing energy to implanted energy consuming components of the apparatus, such as electronic circuits and/or a motor for operating the operation device. The control unit may power such an implanted motor with energy provided by the energizer unit in response to a control signal received from the signal transmitter. Any known or conventional signal transmitting or signal receiving device that is suitable for use with a human or mammal patient may be provided as the signal transmitter or signal receiver. The control signal may comprise an electromagnetic wave signal, such as an infrared light signal, a visible light signal, a laser light signal, a microwave signal, or a sound wave signal, such as an ultrasonic wave signal or an infrasonic wave signal, or any other type of wave signals. The control signal may also comprise electric or magnetic fields, or pulses. All of the above-mentioned signals may comprise digital signals. The control signals may be carried by a carrier signal, which may be the same as the wireless energy signal. Preferably, a digital control signal may be carried by an electromagnetic wave signal. The carrier signal or control signal may be amplitude or frequency modulated.

The motor may be any type of motor, such as a pneumatic, hydraulic or electric motor and the energizer unit may power the motor with pressurized gas or liquid, or electric energy, depending on the type of motor. Where the motor is an electric motor, it may power pneumatic or hydraulic equipment. In all embodiments a motor may be operatively connected to the adjustment device and the control of the motor may be effected by a reversing device implanted in the patient for reversing the function performed by the motor. The reversing device implanted in the patient may also reverse the function performed by the restriction device.

The adjustment device preferably in all embodiments adjusts the restriction device in a non-manual manner without touching the skin of the patient.

The energizer unit may comprise a power supply and the control unit may power the motor with energy from the power supply. Preferably, the power supply is an electric power supply, such as a battery, and the motor is an electric motor. In this case, the battery also continuously powers the circuitry of the signal receiver between the adjustment operations, in order to keep the signal receiver prepared for receiving signals transmitted from the signal transmitter.

The energizer unit may transfer energy from the control signal, as the latter is transmitted to the signal receiver, into electric energy for powering the implanted electronic components. For example, the energizer unit may transfer the energy from the control signal into direct or alternating current.

In case there is an implanted electric motor for operating the operation device the energizer unit may also power the motor with the transferred energy. Advantageously, the control unit directly powers the electric motor with electric energy, as the energizer unit transfers the signal energy into the electric energy. This embodiment is particularly simple and does not require any recurrent invasive measures for exchanging empty power supplies, such as batteries, that is required in the first embodiment described above.

For adjustment devices of the type that requires more, but still relatively low, power for its operation, the energizer unit may comprise a rechargeable electric power supply for storing the electric energy obtained and the control unit may power the electric motor with energy from the rechargeable electric power supply in response to a control signal received from the signal transmitter. In this case, the rechargeable power supply can be charged over a relatively long time (e.g. a few seconds up to a half hour) without powering the electric motor.

The electric power supply suitably comprises an inexpensive simple capacitor. In this case, the electric motor may be a stepping motor.

The signal transmitter may transmit an electromagnetic signal and the energizer unit may draw radiant energy from the electromagnetic wave signal, as the latter is transmitted to the signal receiver, and transfer the radiant energy into electric energy.

Alternatively, the energizer unit may comprise a battery, an electrically operable switch adapted to connect the battery to the signal receiver in an on mode when the switch is powered and to keep the battery disconnected from the signal receiver in a standby mode when the switch is unpowered, and a rechargeable electric power supply for powering the switch. The control unit may power the electric motor with energy from the battery in response to a control signal received from the signal transmitter, when the switch is in its on mode. Advantageously, the energizer unit may transfer wave energy from the control signal, as the latter is transmitted to the signal receiver, into a current for charging the rechargeable electric power supply, which suitable is a capacitor. Energy from the power supply is then used to change the switch from off (standby mode) to on. This embodiment is suited for adjustment devices of the type that require relatively high power for their operation and has the advantage that the electronic circuitry of the signal receiver does not have to be powered by the battery between adjustments. As a result, the life-time of the battery can be significantly prolonged. The switch may be switched with magnetic, manual or electric energy. Preferable the switch is controlled by wireless energy.

As an example, the signal transmitter may transmit an electromagnetic wave signal and the energizer unit may draw radiant energy from the electromagnetic wave signal, as the latter is transmitted to the signal receiver, and may transfer the radiant energy into the current. The energizer unit suitable comprises a coil of the signal receiver for inducing an alternating current as the electromagnetic wave signal is transmitted through the coil and a rectifier for rectifying the alternating current. The rectified current is used for charging the rechargeable power source.

Alternatively, the signal transmitter and receiver may solely be used for a control signal and a further pair of signal transmitter and receiver may be provided for transferring signal energy to implanted components. By such a double system of signal transmitters and receivers the advantage is obtained that the two systems can be designed optimally for their respective purposes, namely to transmit a control signal and to transfer energy from an energy signal. Accordingly, the apparatus may further comprise an external energy transmitter for transmitting wireless energy, wherein the energizer unit comprises a battery and an operable switch for connecting the battery to the signal receiver in an on mode when the switch is powered and for keeping the battery disconnected from the signal receiver in a standby mode when the switch is unpowered, and the external energy transmitter powers the switch. Suitably, the energy transmitter may directly power the switch with the wireless energy to switch into the on mode.

As should be realized by a skilled person, in many of the above-described embodiments of the invention the adjustment device may be operated by control means or manual manipulation means implanted under the skin of the patient, such as a pump, an electrical switch or a mechanical movement transferring means. In the manual embodiment it is not necessary to use a motor for operating the adjustment device.

In accordance with an alternative aspect of the present invention a hydraulic adjustment device adjusts the restriction device to temporarily squeeze the colon or rectum or the prolongation thereof by means of more than one restriction members to restrict the fecal passageway.

In accordance with a further alternative aspect of the present invention it provides an anal incontinence treatment apparatus, comprising an adjustable restriction device implanted in a patient, who suffers from anal incontinence, the restriction device having two restriction members engaging the colon or rectum or the prolongation thereof of the patient to engage the fecal passageway. An adjustment device adjusts the restriction device to temporarily release the colon or rectum or the prolongation thereof and normally to restrict the fecal passageway, and preferable an electrically powered operation device operates the adjustment device in a non-manual manner.

In accordance with another alternative aspect of the present invention there is provided two holding members, one placed more distal than the other, comprising two at least substantially closed loops may be rotated in opposite direction to each other. With interconnecting material for example flexible bands between the holding members a restriction will occur between the holding members when they are rotated.

The restriction device may in all applicable embodiments have any shape or form and be either hydraulic or non-inflatable.

Preferably the adjustment device may be energised directly with wirelessly transmitted energy from outside the patient's body. Preferable, the implanted energy transfer device transfers wireless energy directly or indirectly into kinetic energy for operation of the restriction device. In another embodiment it would also be possible to use an implanted accumulator or battery and control this implanted energy source from outside the patient's body to supply energy to the adjustment device or other energy consuming parts of the implanted apparatus.

It should be understood that all the applicable embodiments in this application may be combined to achieve alternative embodiments of the invention.

The above described embodiments according to the general aspect of the invention may also be implemented in the described embodiments according to the alternative aspects of the invention, where applicable.

The invention also provides a method for treating a patient suffering from anal incontinence comprising surgically implanting in the body of the an adjustable restriction device which directly engages the colon or rectum to restrict the fecal passageway therein, normally closed, and when desired, mechanically adjusting the restriction device to temporarily open the fecal passageway.

The adjustable restriction device may preferably be implanted in the base or prolongation of the patients rectum. It is possible to use one or several restricting devices engaging the colon or rectum.

In accordance with the invention, there is further provided a method for treating anal incontinence, comprising the steps of placing at least two laparascopical trocars in the body of a patient suffering from anal incontinence, inserting a dissecting tool through the trocars and dissecting an area of the colon or rectum in the abdominal or pelvic or retroperitoneal surroundings, placing at least one adjustable restriction device in the dissected area engaging the rectum or colon, adjusting the restriction device to normally restrict the fecal passageway in the rectum or colon, and adjusting the restriction device to open the fecal passageway when the patient wants to relieve himself or herself. A hydraulic adjustable restriction device may be used when practicing this method, preferably in a non-manual manner, i.e. without touching subcutaneously implanted components of the apparatus.

The method may further comprise implanting a source of energy in the patient and providing a control device for controlling the source of energy from outside the patient's body to supply energy to the restriction device.

The present invention also provides a method for treating anal incontinence, comprising surgically implanting in the body of a patient suffering from anal incontinence an adjustable restriction device engaging the colon or rectum or the prolongation thereof to engage the fecal passageway, and when desired to achieve defaecation, adjusting the restriction device to temporarily release the colon or rectum or the prolongation thereof to open the fecal passageway. The method may further comprise implanting an elongated restriction member of the restriction device around the colon or rectum or the prolongation thereof.

In all applications the operation device may be electrically powered.

A further method for treating anal incontinence, comprises surgically implanting in the body of a patient suffering from anal incontinence at least one adjustable restriction devices to affect the fecal passageway engaging respective of the colon or rectum or the prolongation thereof, and when desired to achieve defaecation, non-manually without touching the skin of the patient adjusting the powered restriction device to temporarily release the colon or rectum or the prolongation thereof to open the fecal passageway.

The anal incontinence treatment apparatus may also be laparoscopically implanted. Thus, in accordance with the invention there is also provided a method comprising placing at least two laparascopical trocars in the body of a patient suffering from anal incontinence, inserting a dissecting tool through the trocars, dissecting an area of the pelvic or abdominal or retroperitoneal surroundings, and placing an adjustable restriction device in the dissected area in engagement with the colon, rectum or the prolongation thereof to restrict the fecal passageway.

The adjustment device may preferable be powered preferable with electricity and operated in a non-manual manner without touching the patients skin.

BRIEF DESCRIPTION OF THE DRAWINGS

FIG. 5A is a perspective view of a hydraulic, pneumatic or mechanical servo system in accordance with a particular embodiment of the principal embodiment shown in FIG. 1D.

FIG. 5B is a cross-sectional view taken along line VB-VB of FIG. 5A.

FIGS. 13A through 17B are five modifications of the embodiment of FIGS. 12A-12C.

FIG. 19 illustrates the apparatus of the invention implanted in a patient.

DETAILED DESCRIPTION OF THE DRAWINGS

Figure 1A:
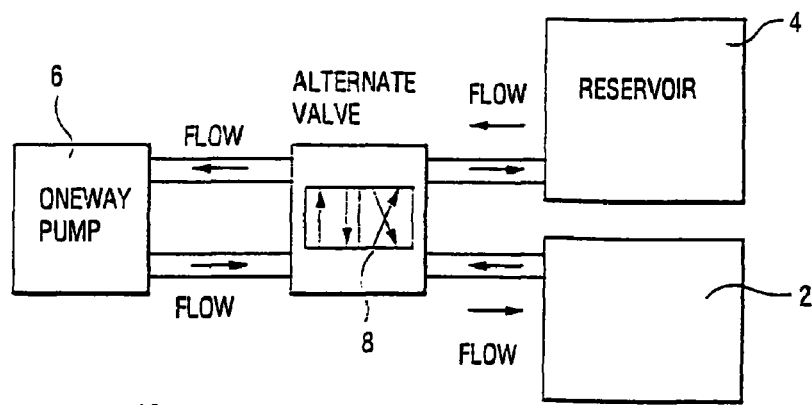
FIGS. 1A-D are block diagrams of four different principal embodiments of the anal incontinence treatment apparatus according to the invention.

Referring to the drawing figures, like reference numerals designate identical or corresponding elements throughout the several figures.

Figure 1B:
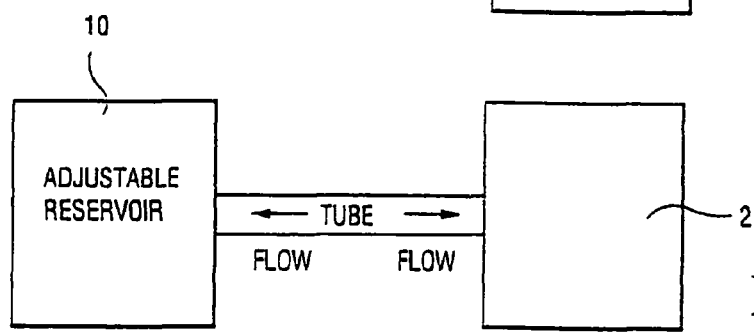
Figure 1C:
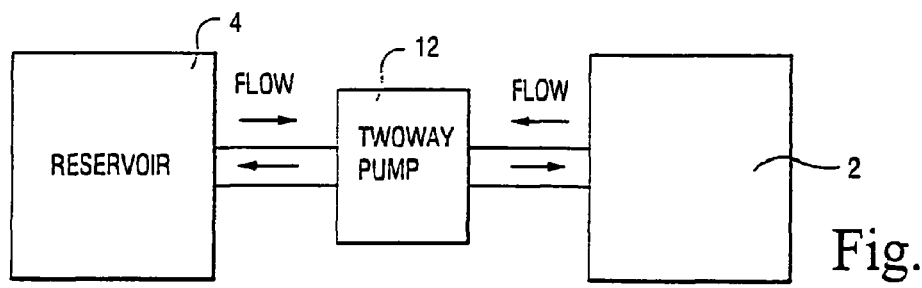
Figure 1D:
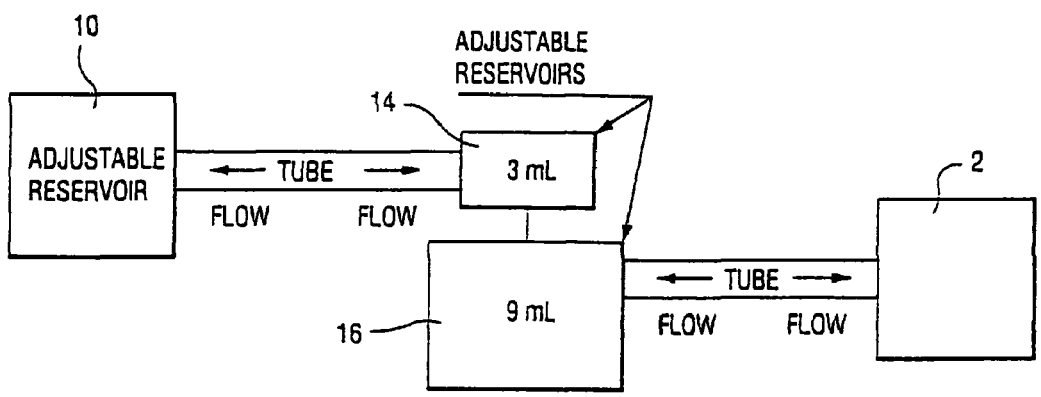
Figure 8:
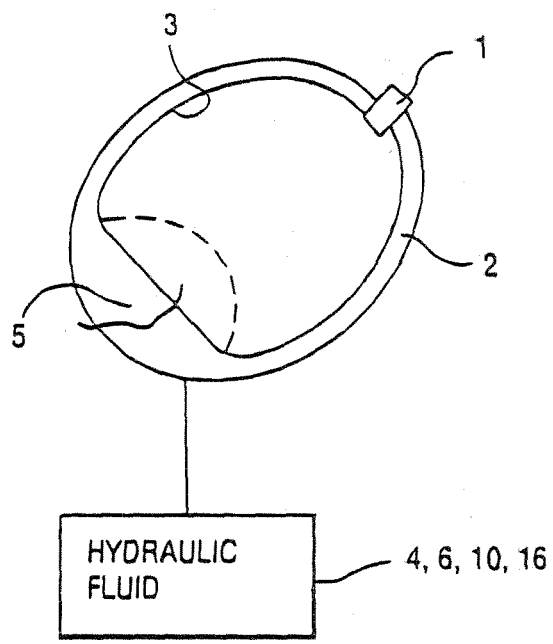
FIG. 8 is a schematic view of a band with a cavity defining a restriction opening for use in accordance with the invention.

FIGS. 1A-D is a block diagram of four different embodiments of the anal incontinence treatment apparatus according to the invention. FIG. 1A shows an elongated restriction member in the form of a band 2 forming a loop which defines a restriction opening. The band 2 provides a restricted fecal passageway in the rectum when applied around the latter. FIG. 1A further shows a separate reservoir 4, a one way pump 6 and an alternate valve 8. FIG. 1B shows the band 2 and a fluid supply reservoir 10. FIG. 1C shows the band 2, a two way pump 12 and the reservoir 4. FIG. 1D shows a servo system with a first closed system controlling a second system. The servo system comprises the fluid supply reservoir 10 and a servo reservoir 14. The servo reservoir 14 controls a larger adjustable reservoir 16 which in connection with the band 2 applied around the rectum varies the volume of a cavity in the band, which in turn varies the restricted fecal passageway in the rectum. Such a band 2 forming the restriction opening 3 is illustrated schematically in FIG. 8. The band 2 comprises an adjustment device having an expandable/contractable cavity 5 which is expanded or contracted by supplying hydraulic fluid (e.g. from reservoir 4, 6, 10, or 16), and the band 2 may be sutured in place, illustrated schematically at 7 in FIG. 8.

Figure 2A:
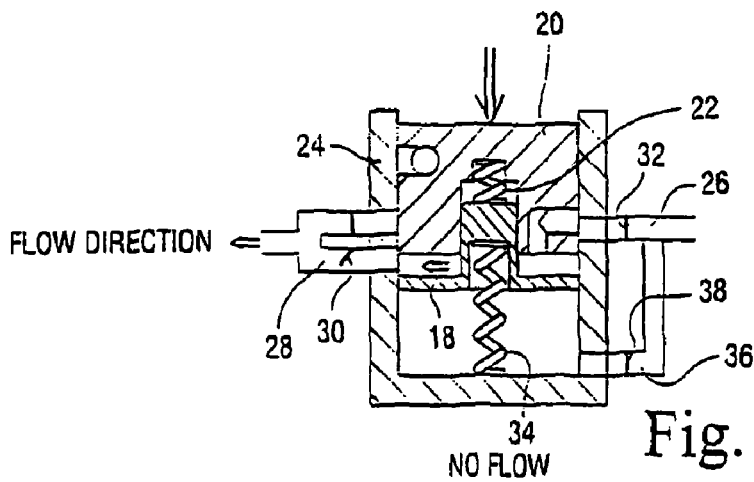
FIG. 2A-D are cross-sectional views of a pump mechanism according to FIG. 1C, which is designed to pump fluid in opposite directions by mechanically pushing a wall portion in only one direction.
Figure 2B:
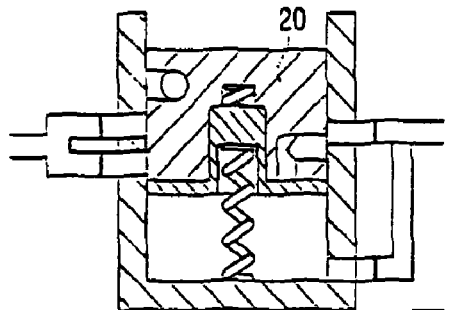
Figure 2C:
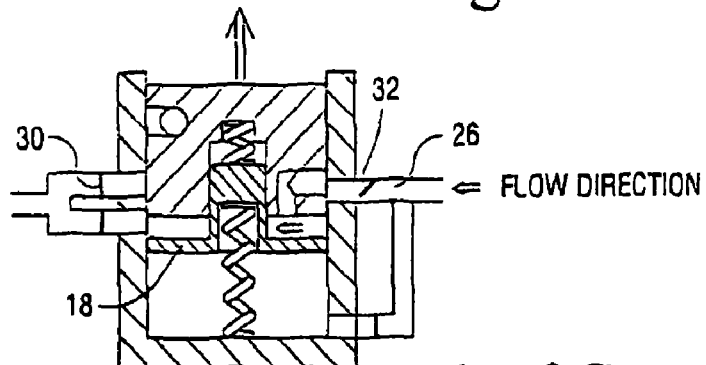
Figure 2D:
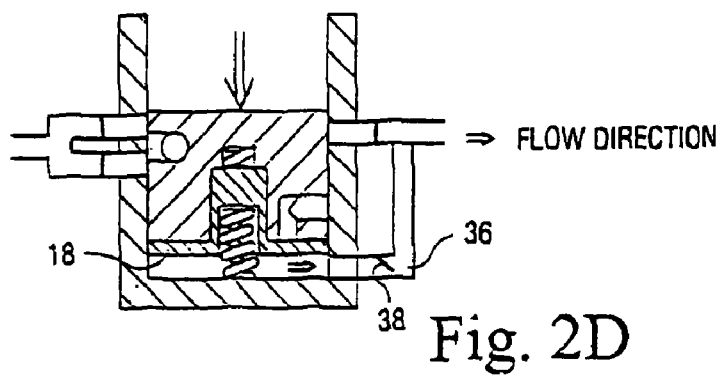

FIGS. 2A-D are cross-sectional views of a pump mechanism adapted to pump fluid in both directions only by mechanically pushing a separate sealing wall portion 18 in one direction. FIG. 2A shows a piston 20 pushed forwards against a spring 22 towards the wall portion 18 and located in a pump housing 24 conducting fluid from a right upper fluid passage 26 of the housing 24 to a left fluid passage 28 of the housing 24. A main valve 30 is open and a nonreturn valve 32 is closed. FIG. 2B illustrates the first pump movement in which the piston 20 has moved forwards and reaches the wall portion 18. FIG. 2C illustrates how the piston 20 moves backwards by the action of the spring 22. The main valve 30 is now closed and the nonreturn valve 32 is open for fluid from the right upper passage 26. FIG. 1D illustrates how the piston 20 is moved further downwards from its position according to FIG. 2B while pushing the wall portion 18 downwardly against a second spring 34 that is stronger than spring 22, whereby fluid escapes from a right lower fluid passage 36. When moving the piston 20 backwardly from the position according to FIG. 2D, fluid enters the left fluid passage 28 and a valve 38 in the lower right fluid passage 36 closes.

Figure 3:
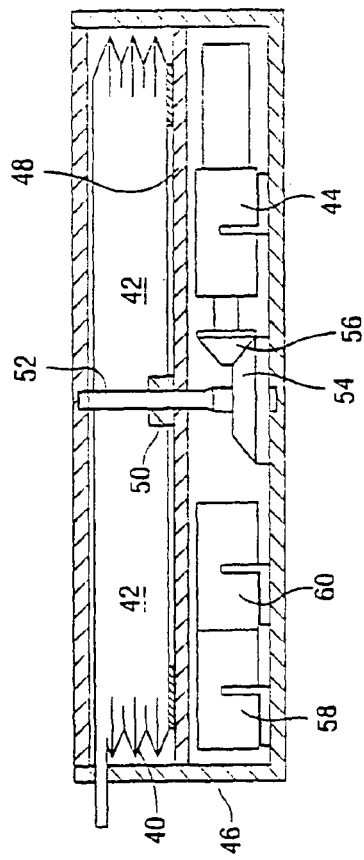
FIG. 3 is a cross-sectional view of a reservoir having a variable volume controlled by a remote control motor, in accordance with a particular embodiment of the principal embodiment shown in FIG. 1B or 2B.

FIG. 3 is a cross-sectional view of a reservoir 40 defining a chamber 42, the size of which is variable and is controlled by a remote controlled electric motor 44, in accordance with FIG. 1B or 1D. The reservoir 40 and the motor 44 are placed in a housing 46. The chamber 42 is varied by moving a large wall 48. The wall 48 is secured to a nut 50, which is threaded on a rotatable spindle 52. The spindle 52 is rotated by the motor 44 via an angular gearing, which comprises two conical gear wheels 54 and 56 in mesh with each other. The motor 44 is powered by a battery 58 placed in the housing 46. An signal receiver 60 for controlling the motor 44 is also placed in the housing 46. Alternatively, the battery 58 and the signal receiver 60 may be mounted in a separate place. The motor 44 may also be powered by energy transferred from transmitted signals.

Figure 4:
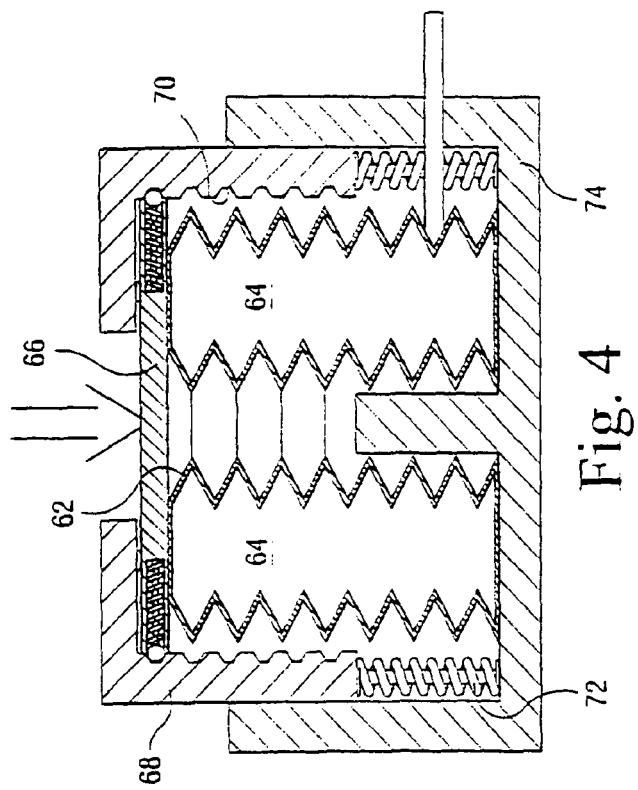
FIG. 4 is a cross-sectional view of a reservoir having a variable volume adjustable by manual manipulation, in accordance with a particular embodiment of the principal embodiment shown in FIG. 1B or 1D.

FIG. 4 is a cross-sectional view of a reservoir 62 defining a chamber 64, the size of which is variable and is controlled by manual manipulation. A gable wall portion 66 of an open ended inner cylindrical housing 68 is adapted to be pushed downwards to fit in a desired locking groove 70 of a plurality of locking grooves 70 on the mantle wall of the cylindrical housing 68, to reduce the size of the chamber 64. The inner cylindrical housing 68 is suspended by springs 72 and is telescopically applied on an outer cylindrical housing 74. When pushing the inner cylindrical housing 68 it moves downwards relative to the outer cylindrical housing 74 causing the gable wall portion 66 to release from the locking groove 70 and move upwards relative to the inner cylindrical housing 68. When the inner housing 68 is moved upwardly by the action of the springs 72 the size of the chamber 64 is increased.

FIGS. 5A and 5B show a servo means comprising a main ring-shaped fluid reservoir 76 defining a chamber 78, the size of which is variable. Centrally positioned in the main ring-shaped reservoir 76 there is a servo fluid reservoir 80 defining a chamber 82, the size of which is variable. The chamber 82 of the servo reservoir 80 is substantially smaller than the chamber 78 of the main reservoir 76. The two reservoirs 76 and 80 are situated between two opposite separate walls 84 and 86, and are secured thereto. When changing the amount of fluid in the servo reservoir 80, the two opposite walls 84, 86 are moved towards or away from each other, whereby the size of the chamber 78 of the main reservoir 76 is changed.

Figure 6:
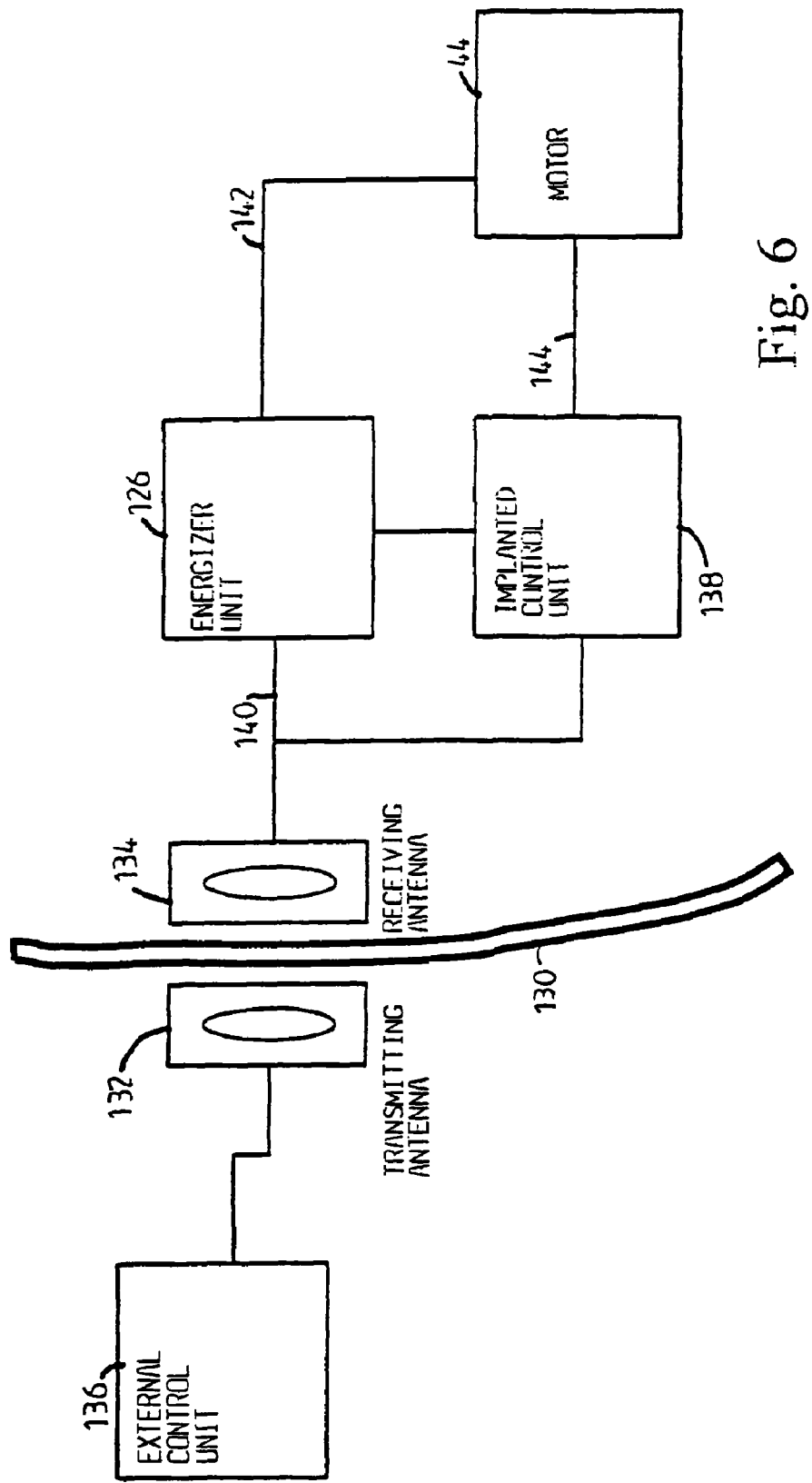
FIG. 6 is a block diagram illustrating remote control components of the device of the invention.

FIG. 6 shows the basic parts of a remote control system of the apparatus of the invention including the electric motor 44 of the embodiment shown in FIG. 3. In this case, the remote control system is based on the transmission of electromagnetic wave signals, often of high frequencies in the order of 100 kHz-1 gHz, through the skin 130 of the patient. In FIG. 6, all parts placed to the left of the skin 130 are located outside the patient's body and all parts placed to the right of the skin 130 are implanted. Any suitable remote control system may be used.

An external signal transmitting antenna 132 is to be positioned close to a signal receiving antenna 134 implanted close to the skin 130. As an alternative, the receiving antenna 134 may be placed for example inside the abdomen of the patient. The receiving antenna 134 comprises a coil, approximately 1-100 mm, preferably 25 mm in diameter, wound with a very thin wire and tuned with a capacitor to a specific high frequency. A small coil is chosen if it is to be implanted under the skin of the patient and a large coil is chosen if it is to be implanted in the abdomen of the patient. The transmitting antenna 132 comprises a coil having about the same size as the coil of the receiving antenna 134 but wound with a thick wire that can handle the larger currents that is necessary. The coil of the transmitting antenna 132 is tuned to the same specific high frequency as the coil of the receiving antenna 134.

An external control unit 136 comprises a microprocessor, a high frequency electromagnetic wave signal generator and a power amplifier. The microprocessor of the control unit 136 is adapted to switch the generator on/off and to modulate signals generated by the generator to send digital information via the power amplifier and the antennas 132,134 to an implanted control unit 138. To avoid that accidental random high frequency fields trigger control commands, digital signal codes are used. A conventional keypad placed on the external control unit 136 is connected to the microprocessor thereof. The keypad is used to order the microprocessor to send digital signals to either increase or decrease the size of the restriction opening defined by the loop of the restriction member 2. The microprocessor starts a command by applying a high frequency signal on the antenna 132. After a short time, when the signal has energized the implanted parts of the control system, commands are sent to increase or decrease the size of the restriction opening of the restriction member 2 in predefined steps. The commands are sent as digital packets in the form illustrated below.

| Start pattern, | Command. | Count. | Checksum, |
|---|---|---|---|
| 8 bits | 8 bits | 8 bits | 8 bits |

The commands are sent continuously during a rather long time period (e.g. about 30 seconds or more). When a new increase or decrease step is desired the Count byte is increased by one to allow the implanted control unit 138 to decode and understand that another step is demanded by the external control unit 136. If any part of the digital packet is erroneous, its content is simply ignored.

Through a line 140, an implanted energizer unit 126 draws energy from the high frequency electromagnetic wave signal received by the receiving antenna 134. The energizer unit 126 stores the energy in a power supply, such as a large capacitor, powers the control unit 138 and powers the electric motor 44 via a line 142.

The control unit 138 comprises a demodulator and a microprocessor. The demodulator demodulates digital signals sent from the external control unit 136. The microprocessor of the control unit 138 receives the digital packet, decodes it and, provided that the power supply of the energizer unit 126 has sufficient energy stored, sends a signal via a signal line 144 to the motor 44 to either increase or decrease the size of the restriction opening of the restriction member 2 depending on the received command code.

Alternatively, the energy stored in the power supply of the energizer unit may only be used for powering a switch, and the energy for powering the motor 44 may be obtained from another implanted power source of relatively high capacity, for example a battery. In this case the switch is adapted to connect the battery to the control unit 138 in an on mode when the switch is powered by the power supply and to keep the battery disconnected from the control unit in a standby mode when the switch is unpowered.

Figure 7:
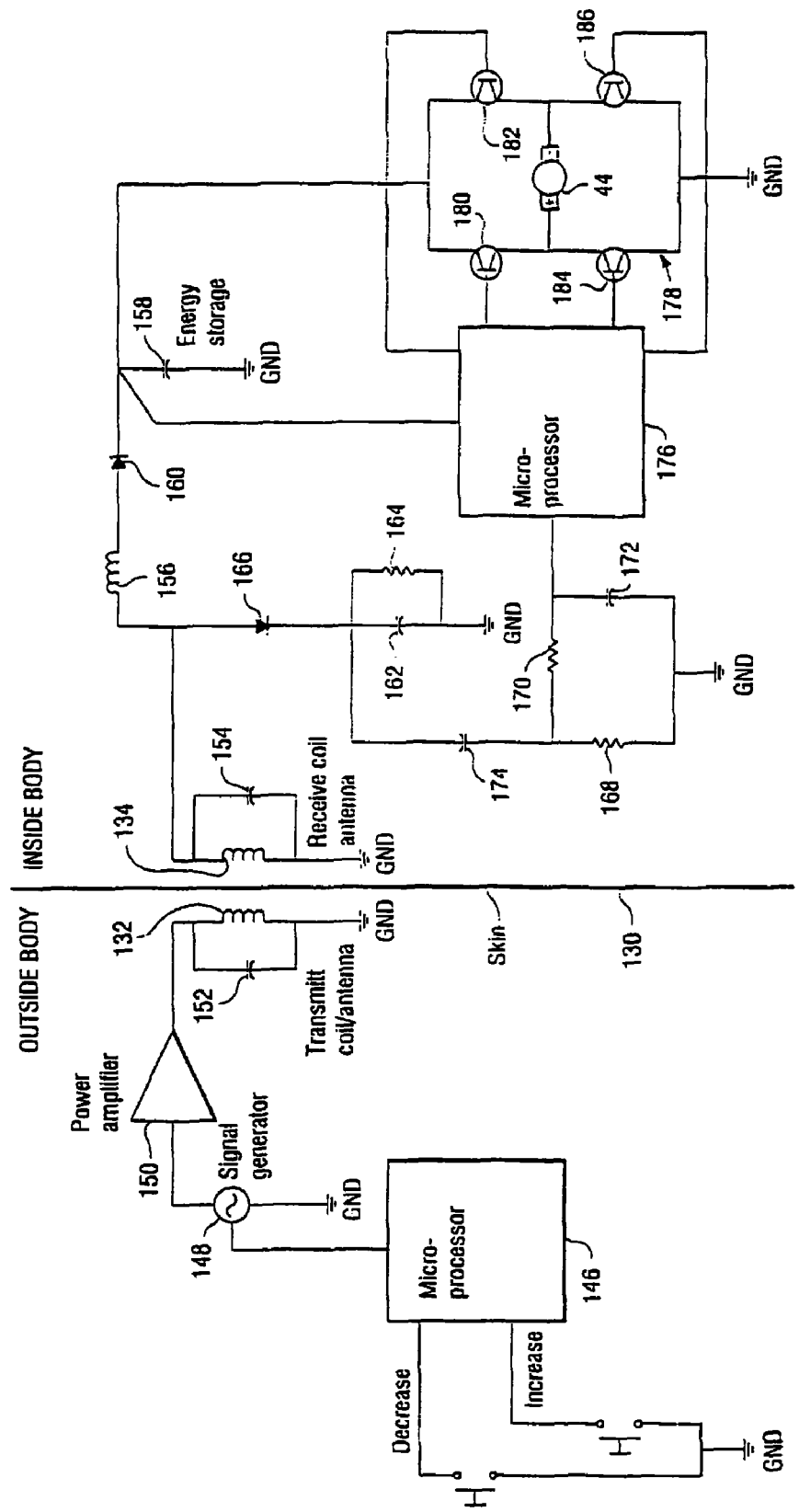
FIG. 7 is a schematic view of exemplary circuitry used for the block diagram in FIG. 4.

With reference to FIG. 7, the remote control system schematically described above will now be described in accordance with a more detailed embodiment. The external control unit 136 comprises a microprocessor 146, a signal generator 148 and a power amplifier 150 connected thereto. The microprocessor 146 is adapted to switch the signal generator 148 on/off and to modulate signals generated by the signal generator 148 with digital commands that are sent to implanted components of the anal incontinence apparatus. The power amplifier 150 amplifies the signals and sends them to the external signal transmitting antenna 132. The antenna 132 is connected in parallel with a capacitor 152 to form a resonant circuit tuned to the frequency generated by the signal generator 148.

The implanted signal receiving antenna coil 134 forms together with a capacitor 154 a resonant circuit that is tuned to the same frequency as the transmitting antenna 132. The signal receiving antenna coil 134 induces a current from the received high frequency electromagnetic waves and a rectifying diode 160 rectifies the induced current, which charges a storage capacitor 158. A coil 156 connected between the antenna coil 134 and the diode 160 prevents the capacitor 158 and the diode 160 from loading the circuit of the signal receiving antenna 134 at higher frequencies. Thus, the coil 156 makes it possible to charge the capacitor 158 and to transmit digital information using amplitude modulation.

A capacitor 162 and a resistor 164 connected in parallel and a diode 166 forms a detector used to detect amplitude modulated digital information. A filter circuit is formed by a resistor 168 connected in series with a resistor 170 connected in series with a capacitor 172 connected in series with the resistor 168 via ground, and a capacitor 174, one terminal of which is connected between the resistors 168,170 and the other terminal of which is connected between the diode 166 and the circuit formed by the capacitor 162 and resistor 164. The filter circuit is used to filter out undesired low and high frequencies. The detected and filtered signals are fed to an implanted microprocessor 176 that decodes the digital information and controls the motor 44 via an H-bridge 178 comprising transistors 180, 182, 184 and 186. The motor 44 can be driven in two opposite directions by the H-bridge 178.

The microprocessor 176 also monitors the amount of stored energy in the storage capacitor 158. Before sending signals to activate the motor 44, the microprocessor 176 checks whether the energy stored in the storage capacitor 158 is enough. If the stored energy is not enough to perform the requested operation, the microprocessor 176 waits for the received signals to charge the storage capacitor 158 before activating the motor 44.

Figure 9A:
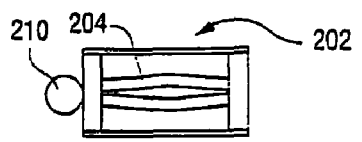
FIGS. 9A and 9B are schematic views of a first mechanical restriction device for use in accordance with the invention.
Figure 9B:
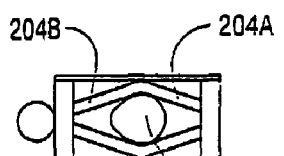

FIGS. 9A and 9B show an embodiment of the apparatus of the invention comprising a restriction device 202 having an elongated flexible restriction member 204, such as a belt, a cord or the like. The flexible member 204 extends in a loop around the rectum. (Alternatively, the flexible member 204 may comprise two separate parts on opposite sides of the rectum.) One portion 204A of member 204 is attached to a frame 208 and another portion 204B of member 204 opposite portion 204A in the loop of the flexible member 204 is connected to an adjustment device 210, which is fixed to the frame 208. The adjustment device 210 pulls the flexible member 204 away from portion 204A to squeeze the rectum between two opposite lengths of the flexible member 204 to thereby restrict the fecal passageway, see FIG. 96A, and releases the rectum from the flexible member 204 to thereby increase the fecal passageway, see FIG. 9B.

Figure 10A:
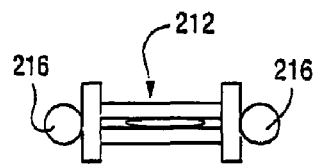
FIGS. 10A and 10B are schematic views of a second mechanical restriction device for use in accordance with the invention.
Figure 10B:
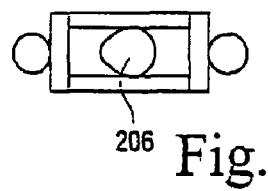

FIGS. 10A and 10B show an embodiment of the apparatus of the invention comprising a restriction device 212 having two plate or bar elements 214 on opposite sides of the rectum 206. An adjustment device 216 moves the elements 212 in parallel towards each other to squeeze the rectum 206 between the elements 212 to thereby restrict the fecal passageway, see FIG. 10A, and moves the elements 212 away from each other to increase the fecal passageway, see FIG. 10B.

Figure 11:
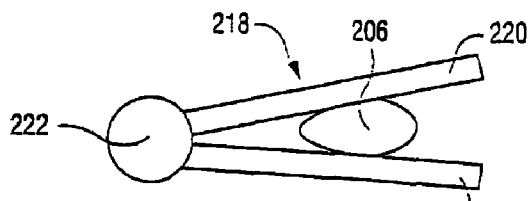
FIG. 11 is a schematic view of a third mechanical restriction device for use in accordance with the invention.

FIG. 11 shows an embodiment of the apparatus of the invention comprising a restriction device 218 having two articulated clamping elements 220 positioned on opposite sides of the rectum 206. An adjustment device 222 moves the clamping elements 220 toward each other to clamp the rectum 206 between the clamping elements 220 to thereby restrict the fecal passageway, and moves the clamping elements 220 away from each other to release the rectum 206 from the clamping elements 220 to thereby increase the fecal passageway.

Figure 12A:
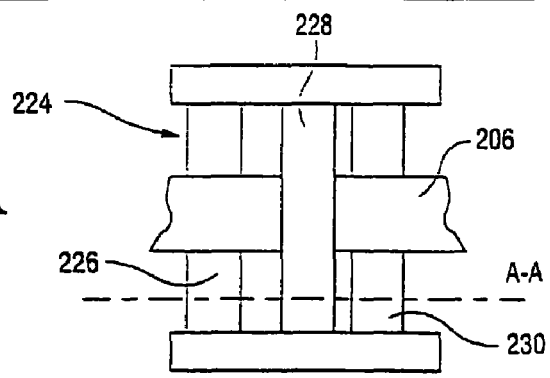
FIG. 12A is a schematic front view of a fourth mechanical restriction device for use in accordance with the invention.
Figure 12B:
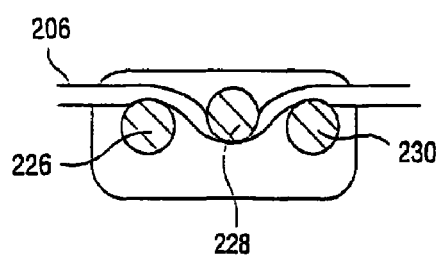
FIGS. 12B and 12C are sectional views along the line A-A of FIG. 12A.
Figure 12C:
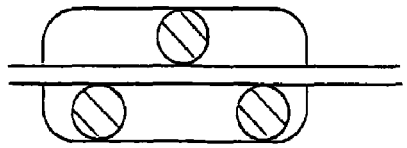
Figure 16A:
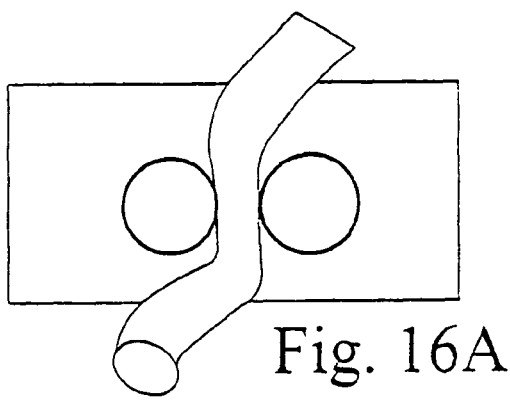
Figure 16B:
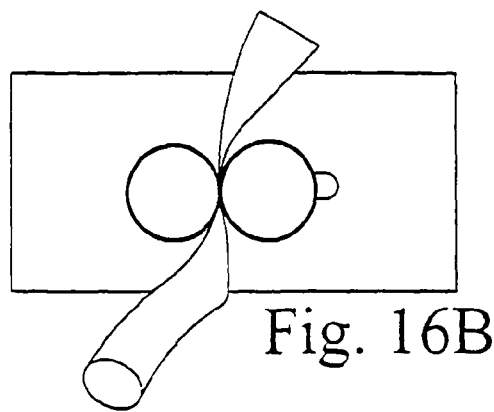

FIGS. 12A, 12B and 12C show an embodiment of the apparatus of the invention comprising a restriction device 224 having three bending members in the form of cylindrical rollers 226, 228 and 230 displaced relative one another in a row along the rectum 206 and positioned alternately on opposite sides of the rectum 206. (Alternatively, each roller 226, 228 and 230 may take the shape of an hour-glass.) An adjustment device 232 moves the two outer rollers 226,230 laterally against the rectum 206 in one direction and the intermediate roller 228 against the rectum 206 in the opposite direction to bend the rectum to thereby restrict the fecal passageway, see FIG. 12B. To release the rectum from the rollers 226-230, the adjustment device 232 moves the rollers 226-230 away from the rectum 206, see FIG. 12C.

Figure 17A:
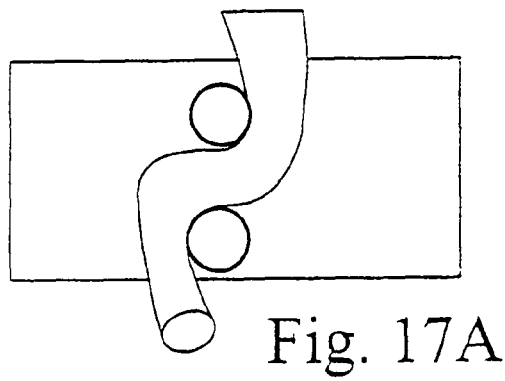
Figure 17B:
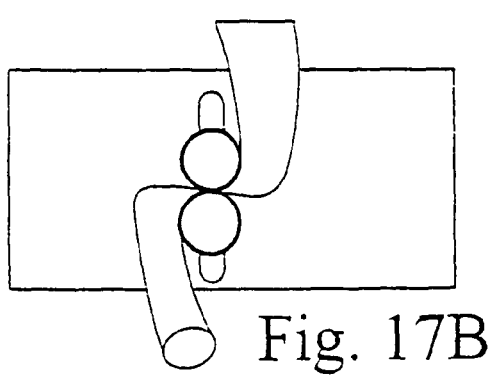

FIGS. 13A through 17B schematically illustrates modification of the above embodiment according to FIGS. 12A-12C. Thus, FIGS. 13A and 13B show an embodiment similar to that of FIGS. 12A-12C except that the bending members are oval and not rotatable. FIGS. 14A and 14B show an embodiment similar to that of FIGS. 13A and 13B except that the oval bending members are rotatable to squeeze the rectum, see FIG. 14B, and to release the rectum, see FIG. 14A. FIGS. 15A and 15B show an embodiment similar to that of FIGS. 12A-12C except that the intermediate roller has a changeable diameter to squeeze the rectum, see FIG. 15B, and to release the rectum, see FIG. 15A. FIGS. 16A and 16B show an embodiment similar to that of FIGS. 10A-10C except that the elements are replaced by two cylindrical rollers positioned on opposite sides of the rectum. Finally, FIGS. 17A and 17B show an embodiment substantially similar to that of FIGS. 16A and 16B except that the restriction device is turned 90 to form a S-shaped curvature of the rectum.

Figure 18:
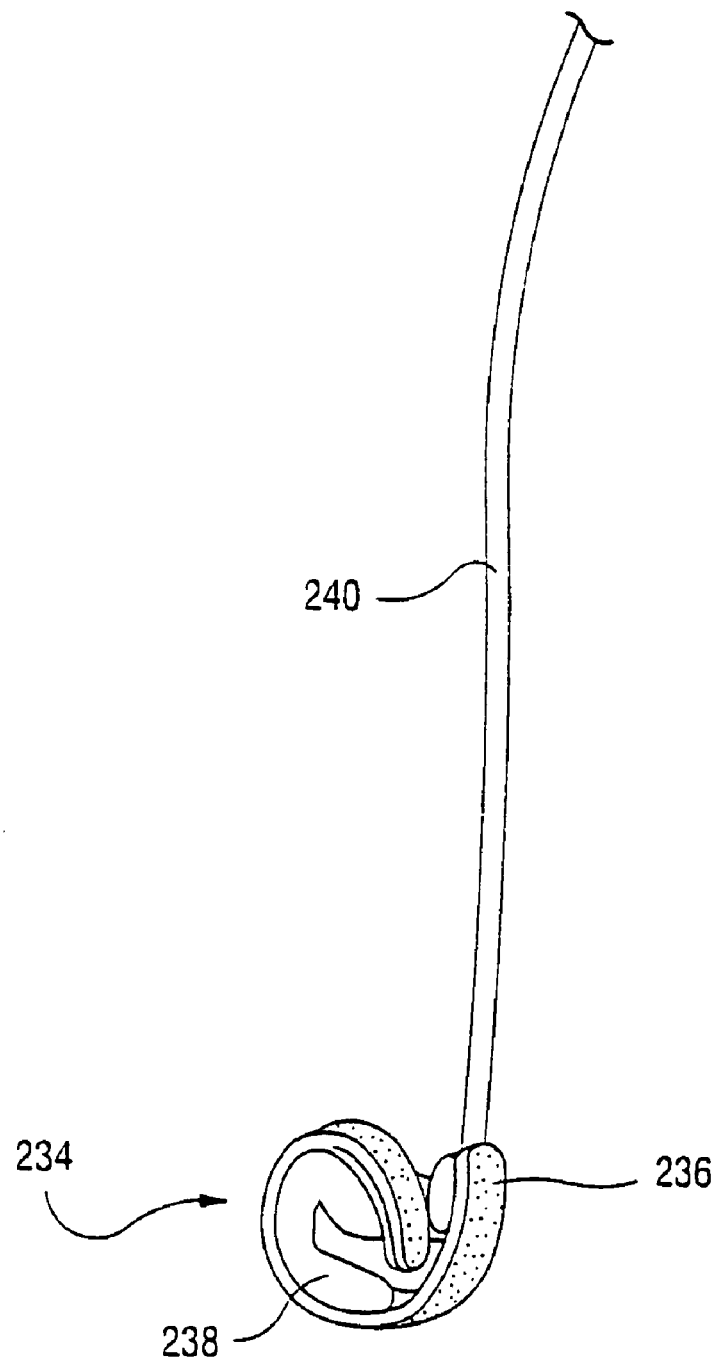
FIG. 18 is a view of an inflatable restriction device of the apparatus of the invention.

FIG. 18 shows an example of a hydraulic restriction device 234 for use in accordance with the invention. The restriction device 234 comprises an elongated restriction member 236 having an inflatable cavity 238. A tube 240 connects the cavity 238 to a hydraulic fluid reservoir, not shown. The restriction member 236 may be wrapped around the rectum.

FIG. 19 schematically illustrates how any of the above-described embodiments of the anal incontinence treatment apparatus of the invention can be implanted in a patient. Thus, an implanted adjustable hydraulic restriction device 234 extends almost completely around the rectum 242 to be capable of squeezing the rectum 242 as a single unit. An adjustment device in the form of an inflatable cavity in the restriction device 234 is adapted to adjust the restriction device 234 so that the fecal passageway is restricted. An implanted assembly 246 includes a hydraulic fluid reservoir and an operation device (which may include a pump) for distributing hydraulic fluid between the reservoir and the inflatable/contractible cavity of the restriction device 234 via a fluid conduit 240. A wireless remote control of the apparatus comprises an external signal transmitter 248, which may comprise a hand-held unit, and an implanted signal receiver, which is incorporated in the implanted assembly 246, includes a control unit for controlling the restriction device 234 in response to a control signal from the external transmitter. The signal receiver of the assembly 246 further includes an energizer unit which transfers energy from the control signal transmitted by the external transmitter into electric energy for energy consuming implanted components of the apparatus.

A pressure sensor 250 is implanted for sensing the pressure on the restriction device 234. The control unit of the signal receiver of the implanted assembly 246 controls the restriction device 436 to release the restriction device 434 in response to the pressure sensor 439 sensing an abnormal high pressure.

There are a number of conceivable alternative embodiments of the invention that give the same result as the above-described embodiments. For example, the microprocessor of the external and implanted, respectively, control units may be replaced by discrete components. The power amplifier of the external control unit may be omitted if the signals generated by the signal generator are strong enough. Therefore, the invention is to be accorded the broadest interpretation of the appended claims to encompass all equivalent structures and assemblies.

What is claimed is:

1. An anal incontinence disease treatment apparatus, comprising:
    an operable restriction device adapted to be implanted in a patient to engage the colon or rectum or the prolongation thereof to form a restricted fecal passageway in the colon or rectum or the prolongation thereof,
    an energy transmission device for wireless transmission of energy from outside the patient's body,
    an energy transfer device adapted to be implanted in the patient for transferring energy transmitted by said energy transmission device into a different form energy, said restriction device being operable in response to said different form energy to vary the restriction of the restricted fecal passageway, and
    an operation device adapted to be implanted in the patient for operating said restriction device,
    wherein said different form energy is used for powering said operation device to operate said restriction device to close the fecal passageway to prevent feces to pass therethrough and to enlarge the fecal passageway to allow feces to readily pass therethrough.

2. An apparatus according to claim 1, wherein said energy transfer device is capable of supplying a direct current, a pulsating direct current or a combination of a direct current and pulsating direct current via conductors connected to said energy transfer device.

3. An apparatus according to claim 1, wherein said operation device comprises a linear motor.

4. An apparatus according to claim 1, further comprising a control device, and wherein said operation device comprises a hydraulic or pneumatic fluid motor, and said control device controls the said fluid motor.

5. An apparatus according to claim 1, wherein said restriction device comprises hydraulic means and said operation device comprises a pump for pumping a fluid in said hydraulic means.

6. An apparatus according to claim 5, wherein said operation device comprises a motor for driving said pump.

7. An apparatus according to claim 5, wherein said operation device comprises a fluid conduit between said pump and said hydraulic means of said restriction device, and a reservoir for fluid, said reservoir forming part of said conduit.

8. An apparatus according to claim 7, wherein said hydraulic means, pump and conduit is devoid of any non-return valve.

9. An apparatus according to claim 8, wherein said reservoir forms a fluid chamber with a variable volume, and said pump distributes fluid from said chamber to said hydraulic means of said restriction device by reduction of the volume of said chamber and withdraws fluid from said hydraulic means to said chamber by expansion of the volume of said chamber.

10. An apparatus according to claim 1, wherein said restriction device is operable to perform a reversible function.

11. An apparatus according to claim 1, wherein the energy transmitted by said energy transmission device comprises a magnetic field.

12. An apparatus according to claim 11, wherein said magnetic field is transmitted in pulses or digital pulses, or a combination of pulses and digital pulses by said energy transmission device.

13. An apparatus according to claim 1, wherein said energy transfer device transfers the energy transmitted by said energy transmission device into a direct current or pulsating direct current, or a combination of a direct current and a pulsating direct current.

14. An apparatus according to claim 1, wherein said energy transfer device transfers the energy transmitted by said energy transmission device into an alternating current or a combination of a direct and alternating current.

15. An apparatus according to claim 1, wherein said different form energy comprises a frequency or amplitude modulated signal, or a combination of a frequency and amplitude modulated signal.

16. An apparatus according to claim 1, wherein said different form energy comprises an analog or a digital signal, or a combination of an analog and digital signal.

17. An apparatus according to claim 1, wherein said operation device comprises hydraulic means and at least one valve for controlling a fluid flow in said hydraulic means.

18. An apparatus according to claim 17, further comprising a wireless remote control for controlling said valve.

19. An apparatus according to claim 1, wherein said restriction device is non-inflatable.

20. An apparatus according to claim 1, wherein one of the energy transmitted by said energy transmission device and said different form energy comprises kinetic energy.

21. An anal incontinence disease treatment apparatus, comprising:
an operable restriction device adapted to be implanted in a patient to engage the colon or rectum or the prolongation thereof to form a restricted fecal passageway in the colon or rectum or the prolongation thereof,
an energy transmission device for wireless transmission of energy from outside the patient's body,
an energy transfer device adapted to be implanted in the patient for transferring energy transmitted by said energy transmission device into a different form energy,
an energy storage device adapted to be implanted in the patient for storing said different form energy and for supplying energy for operation of said restriction device, and
a switch adapted to be implanted in the patient for directly or indirectly switching the supply of energy from said energy storage device, and
an operation device adapted to be implanted in the patient for operating said restriction device,
wherein said switch is inoperable by permanent magnets, and
wherein said restriction device comprises hydraulic means and said operation device comprises a pump for pumping a fluid in said hydraulic means.

22. An anal incontinence disease treatment apparatus, comprising:
an operable restriction device adapted to be implanted in a patient to engage the colon or rectum or the prolongation thereof to form a restricted fecal passageway in the colon or rectum or the prolongation thereof,
an energy transmission device for wireless transmission of energy from outside the patient's body,
an energy transfer device adapted to be implanted in the patient for transferring energy transmitted by said energy transmission device into a different form energy,
wherein said restriction device is adapted to be directly operated to vary the restriction of the restricted fecal passageway, in response to said different form energy transferred by said energy transfer device, as said energy transmission device transmits energy, and
wherein said restriction device is operable to perform a reversible function.

23. An apparatus according to claim 22, wherein said restriction device comprises hydraulic means and said operation device comprises a pump for pumping a fluid in said hydraulic means.

24. An anal incontinence disease treatment apparatus, comprising:
an operable restriction device adapted to be implanted in a patient to engage the colon or rectum or the prolongation thereof to form a restricted fecal passageway in the colon or rectum or the prolongation thereof,
a source of energy external to the patient's body,
a control device operable from outside the patient's body for releasing wireless energy from said source of energy without the use of permanent magnets, and
an energy transfer device for transferring the released wireless energy into an energy form suited for use in connection with the operation of said restriction device.

25. An apparatus according to claim 24, wherein said restriction device is non-inflatable.

26. An anal incontinence disease treatment apparatus, comprising:
an operable restriction device adapted to be implanted in a patient to engage the colon or rectum or the prolongation thereof to form a restricted fecal passageway in the colon or rectum or the prolongation thereof,
a source of energy external to the patient's body, and
a control device operable from outside the patient's body for releasing wireless energy from said source of energy and transferring said released wireless energy into electric energy to be used in connection with the operation of said restriction device.

27. An apparatus according to claim 26, wherein said control device releases energy from said source of energy in a non-invasive manner.

28. An apparatus according to claim 26, wherein said control device releases magnetic energy.

29. An apparatus according to claim 26, wherein said control device releases electromagnetic energy.

30. An apparatus according to claim 26, wherein said control device releases kinetic energy.

31. An apparatus according to claim 26, wherein said control device releases energy from said source of energy in a mechanical manner.

32. An apparatus according to claim 26, wherein said control device releases non-magnetic energy.

33. An apparatus according to claim 26, wherein said control device releases non-electromagnetic energy.

34. An apparatus according to claim 26, wherein said control device releases non-kinetic energy.

35. An apparatus according to claim 26, wherein said control device releases or non-thermal energy.

36. An apparatus according to claim 26, wherein said control device releases energy from said source of energy in a non-mechanical manner.

37. An apparatus according to claim 26, wherein said control device directly powers said operation device with energy released from said source of energy and/or powers other implanted energy consuming components of the apparatus.

38. An apparatus according to claim 26, further comprising a motor implanted in the patient for operating said restriction device.

39. An apparatus according to claim 38, wherein said motor mechanically operates said restriction device.

40. An apparatus according to claim 26, further comprising a pump implanted in the patient for operating said restriction device.

41. An apparatus according to claim 40, wherein said pump hydraulically operates said restriction device.

42. An apparatus according to claim 26, wherein said restriction device is non-inflatable.

43. An apparatus according to claim 13, wherein said restriction device is non-inflatable.

44. An anal incontinence disease treatment apparatus, comprising:
   an operable restriction device adapted to be implanted in a patient to engage the colon or rectum or the prolongation thereof to form a restricted fecal passageway in the colon or rectum or the prolongation thereof,
   a source of energy,
   a control device operable from outside the patient's body for releasing energy from said source of energy, said released energy being used in connection with the operation of said restriction device,
   a switch implantable in the patient for directly or indirectly switching said energy released from said source of energy, and
   an energy transfer device for transferring wireless energy into an energy form suited for operating said switch.

45. An apparatus according to claim 1, wherein said restriction device is non-inflatable.

46. An anal incontinence disease treatment apparatus, comprising:
   an operable restriction device adapted to be implanted in a patient to engage the colon or rectum or the prolongation thereof to form a restricted fecal passageway in the colon or rectum or the prolongation thereof,
   a source of energy adapted to be implanted in the patient for supplying energy to be used in connection with the operation of said restriction device,
   an energy transfer device for transferring wireless energy into an energy form suited for charging said source of energy,
   a control device operable from outside the patient's body to control said energy transfer device to charge said source of energy with transferred wireless energy,
   wherein said control device comprises a wireless remote control transmitting at least one wireless control signal for controlling said restriction device and an internal control unit adapted to be implanted in the patient for receiving the wireless control signal, and
   wherein said restriction device is non-inflatable.

47. An anal incontinence disease treatment apparatus, comprising:
   an operable restriction device adapted to be implanted in a patient to engage the colon or rectum or the prolongation thereof to form a restricted fecal passageway in the colon or rectum or the prolongation thereof,
   an implantable powered operation device for operating said restriction device,
   a source of energy external to the patient's body,
   a control device operable from outside the patient's body to control said external source of energy to release wireless energy,
   an implantable energy transfer device adapted to transfer said wireless energy into storable energy, and
   an implantable internal source of energy adapted to store said storable energy and power said operation device with said storable energy,
   wherein said control device controls said restriction device to close the fecal passageway to prevent feces from passing therethrough and enlarge the fecal passageway to allow feces to readily pass therethrough, and
   wherein said operation device comprises hydraulic means and at least one valve for controlling a fluid flow in said hydraulic means.

48. An apparatus according to claim 47, wherein said control device comprises a wireless remote control for controlling said valve.

49. An apparatus according to claim 47, wherein said restriction device comprises hydraulic means and said operation device comprises a reservoir forming a fluid chamber with a variable volume connected to said hydraulic means, and said operation device distributes fluid from said chamber to said hydraulic means by reduction of the volume of said chamber and withdraws fluid from said hydraulic means to said chamber by expansion of the volume of said chamber.

50. An apparatus according to claim 47, wherein said wireless energy is directly used for operation of said restriction device in a non-magnetic manner.

51. An apparatus according to claim 47, wherein said operation device comprises a hydraulic or pneumatic fluid motor, and said control device controls the fluid flow through said fluid motor.

52. An apparatus according to claim 47, wherein said restriction device comprises hydraulic means and said operation device comprises a pump for pumping a fluid in said hydraulic means.

53. An apparatus according to claim 52, wherein said operation device comprises a motor for driving said pump.

54. An apparatus according to claim 53, wherein said operation device comprises a fluid conduit between said pump and said hydraulic means of said restriction device, and a reservoir for fluid, said reservoir forming part of said conduit.

55. An apparatus according to claim 54, wherein said hydraulic means, pump and conduit are devoid of any non-return valve.

56. An apparatus according to claim 55, wherein said reservoir forms a fluid chamber with a variable volume, and said pump distributes fluid from said chamber to said hydraulic means of said restriction device by reduction of the volume of said chamber and withdraws fluid from said hydraulic means to said chamber by expansion of the volume of said chamber.

57. An apparatus according to claim 52, wherein said operation device comprises a motor for driving said pump.

58. An apparatus according to claim 57, wherein said operation device comprises a fluid conduit between said pump and said hydraulic means of said restriction device, and a reservoir for fluid, said reservoir forming part of said conduit.

59. An apparatus according to claim 58, wherein said hydraulic means, pump and conduit is devoid of any non-return valve.

60. An apparatus according to claim 59, wherein said reservoir forms a fluid chamber with a variable volume, and said pump distributes fluid from said chamber to said hydraulic means of said restriction device by reduction of the volume of said chamber and withdraws fluid from said hydraulic means to said chamber by expansion of the volume of said chamber.

61. An apparatus according to claim 47, wherein said restriction device is non-inflatable.

62. An apparatus according to claim 47, wherein said control device releases magnetic energy.

63. An apparatus according to claim 47, wherein said control device releases kinetic energy.

64. An apparatus according to claim 47, wherein said control device releases energy from said external source of energy in a mechanical manner.

65. An apparatus according to claim 47, wherein said control device releases non-magnetic energy.

66. An apparatus according to claim 47, wherein said control device releases non-electromagnetic energy.

67. An apparatus according to claim 47, wherein said control device releases non-kinetic energy.

68. An apparatus according to claim 47, wherein said control device releases non-thermal energy.

69. An anal incontinence disease treatment apparatus, comprising:
an operable restriction device adapted to be implanted in a patient to engage the colon or rectum or the prolongation thereof to form a restricted fecal passageway,
an implantable powered operation device for operating said restriction device,
a source of energy external to the patient's body,
a control device operable from outside the patient's body to control said external source of energy to release non-magnetic wireless energy for use in the powering of said operation device,
an implantable energy transfer device for transferring said non-magnetic wireless energy into another form of energy usable by said operation device,
wherein said control device controls said restriction device to close the fecal passageway to prevent feces from passing therethrough and enlarge the fecal passageway to allow feces to readily pass therethrough.

70. An apparatus according to claim 69, wherein said control device comprises an internal control unit implantable in the patient for controlling said restriction device.

71. An apparatus according to claim 70, wherein said internal control unit comprises a microprocessor.

72. An apparatus according to claim 69, wherein said restriction device comprises hydraulic means and said operation device comprises a reservoir forming a fluid chamber with a variable volume connected to said hydraulic means, and said operation device distributes fluid from said chamber to said hydraulic means by reduction of the volume of said chamber and withdraws fluid from said hydraulic means to said chamber by expansion of the volume of said chamber.

73. An apparatus according to claim 69, wherein said non-magnetic wireless energy released from said external source of energy is directly, during energy transfer, used for operation of said restriction device.

74. An apparatus according to claim 73, wherein said wireless energy, directly or indirectly powers said operation device.

75. An apparatus according to claim 73, wherein said operation device comprises a motor.

76. An apparatus according to claim 75, wherein said motor comprises a rotary motor, and said control device controls said rotary motor to rotate a desired number of revolutions.

77. An apparatus according to claim 75, wherein said motor comprises a linear motor.

78. An apparatus according to claim 75, wherein said motor comprises a hydraulic or pneumatic fluid motor, and said control device controls the fluid flow through said fluid motor.

79. An apparatus according to claim 73, wherein said restriction device is operable by said operation device to perform a reversible function.

80. An apparatus according to claim 79, further comprising a reversing device implantable in the patient for reversing said function performed by said restriction device.

81. An apparatus according to claim 80, wherein said control device controls said reversing device to reverse said function performed by said restriction device.

82. An apparatus according to claim 80, wherein said operation device comprises a motor, and said reversing device reverses said motor.

83. An apparatus according to claim 73, wherein said restriction device comprises hydraulic means and said operation device comprises a pump for pumping a fluid in said hydraulic means.

84. An apparatus according to claim 83, wherein said operation device comprises a motor for driving said pump.

85. An apparatus according to claim 84, wherein said operation device comprises a fluid conduit between said pump and said hydraulic means of said restriction device, and a reservoir for fluid, said reservoir forming part of said conduit.

86. An apparatus according to claim 85, wherein said hydraulic means, pump and conduit are devoid of any non-return valve.

87. An apparatus according to claim 86, wherein said reservoir forms a fluid chamber with a variable volume, and said pump distributes fluid from said chamber to said hydraulic means of said restriction device by reduction of the volume of said chamber and withdraws fluid from said hydraulic means to said chamber by expansion of the volume of said chamber.

88. An apparatus according to claim 69, further comprising a switch implantable in the patient for directly or indirectly switching the operation of said restriction device.

89. An apparatus according to claim 69, further comprising at least one implantable sensor for sensing at least one physical parameter of the patient.

90. An apparatus according to claim 89, wherein said control device controls said restriction device in response to signals from said sensor.

91. An apparatus according to claim 90, wherein said control device comprises an internal control unit implantable in the patient, said internal control unit controlling said restriction device in response to signals from said sensor.

92. An apparatus according to claim 89, wherein said control device comprises an external control unit that stores information on said physical parameter sensed by said sensor and is manually operated to control said restriction device based on said stored information.

93. An apparatus according to claim 69, wherein said restriction device is non-inflatable.

94. An apparatus according to claim 69, wherein said control device comprises a wireless remote control transmitting at least one wireless control signal for controlling said restriction device.

95. An apparatus according to claim 94, wherein said remote control is capable of sending information related to said restriction device from inside the patient's body to the outside thereof.

96. An apparatus according to claim 94, wherein said control signal comprises a wave signal comprising one of a sound wave signal including an ultrasound wave signal, an electromagnetic wave signal including an infrared light signal, a visible light signal, an ultra violet light signal and a laser light signal, a micro wave signal, a radio wave signal, an x-ray radiation signal, and a gamma radiation signal.

97. An apparatus according to claim 94, wherein said control signal comprises an electric, magnetic or electric and magnetic field.

98. An apparatus according to claim 94, wherein said control signal is digital, analog or digital and analog.

99. An apparatus according to claim 69, wherein said control device releases energy from said external source of energy in a non-invasive manner.

100. An apparatus according to claim 69, wherein said control device releases non-thermal energy.

101. An apparatus according to claim 69, wherein said non-magnetic wireless energy comprises an electric field.

102. An apparatus according to claim 69, wherein said non-magnetic wireless energy is in the form of a digital, analog or digital and analog signal.

103. An apparatus according to claim 70, wherein said non-magnetic wireless energy comprises a wave signal, a sound signal or an ultrasound wave signal.

104. An anal incontinence disease treatment apparatus, comprising:
an operable restriction device adapted to be implanted in a patient to engage the colon or rectum or the prolongation thereof to form a restricted fecal passageway,
an implantable powered operation device for operating said restriction device,
a source of energy external to the patient's body,
a control device operable from outside the patient's body to control said external source of energy to release electromagnetic wireless energy for use in the powering of said operation device,
an implantable energy transfer device for transferring said electromagnetic wireless energy into another form of energy usable by said operation device,
wherein said control device controls said restriction device to close the fecal passageway to prevent feces from passing therethrough and enlarge the fecal passageway to allow feces to readily pass therethrough, and
wherein said control device comprises an internal control unit implantable in the patient for controlling said restriction device.

105. An apparatus according to claim 104, wherein said restriction device comprises hydraulic means and said operation device comprises a reservoir forming a fluid chamber with a variable volume connected to said hydraulic means, and said operation device distributes fluid from said chamber to said hydraulic means by reduction of the volume of said chamber and withdraws fluid from said hydraulic means to said chamber by expansion of the volume of said chamber.

106. An apparatus according to claim 104, wherein said operation device comprises a hydraulic or pneumatic fluid motor, and said control device controls the fluid flow through said fluid motor.

107. An apparatus according to claim 104, wherein said restriction device is operable by said operation device to perform a reversible function, and said apparatus further comprises a reversing device implantable in the patient for reversing said function performed by said restriction device, and
wherein said operation device comprises a motor, and said reversing device reverses said motor.

108. An apparatus according to claim 104, wherein said restriction device comprises hydraulic means and said operation device comprises a pump for pumping a fluid in said hydraulic means.

109. An apparatus according to claim 106, wherein said operation device comprises a motor for driving said pump.

110. An apparatus according to claim 109, wherein said operation device comprises a fluid conduit between said pump and said hydraulic means of said restriction device, and a reservoir for fluid, said reservoir forming part of said conduit.

111. An apparatus according to claim 110, wherein said hydraulic means, pump and conduit are devoid of any non-return valve.

112. An apparatus according to claim 111, wherein said reservoir forms a fluid chamber with a variable volume, and said pump distributes fluid from said chamber to said hydraulic means of said restriction device by reduction of the volume of said chamber and withdraws fluid from said hydraulic means to said chamber by expansion of the volume of said chamber.

113. An apparatus according to claim 104, wherein said restriction device is non-inflatable.

114. An apparatus according to claim 104, further comprising an implantable energy transfer device adapted to transfer said wireless energy into non-thermal energy.

115. An apparatus according to claim 104, wherein said electromagnetic wireless energy comprises an electromagnetic field.

116. An apparatus according to claim 104, wherein said electromagnetic wireless energy is in the form of a digital, analog or digital and analog signal.

117. A method of treating a human or animal having anal incontinence disease, comprising:
(a) surgically implanting in the human or animal an operable restriction device engaging the human's or animal's colon or rectum or the prolongation thereof to form a restricted fecal passageway,
(b) providing a source of energy external to the patient's body,
(c) controlling the external source of energy from outside the patient's body to release non-magnetic wireless energy,
(d) transferring said non-magnetic wireless energy into a different form of energy,
(e) using the different form of energy to operate the restriction device, and
(f) controlling the restriction device to restrict the fecal passageway to prevent feces from passing therethrough and enlarge the fecal passageway to allow feces to readily pass therethrough.

* * * * *